(12) United States Patent
Lunyak

(10) Patent No.: US 8,981,066 B2
(45) Date of Patent: Mar. 17, 2015

(54) EPIGENETIC MECHANISMS RELATED TO DNA DAMAGE AND AGING

(75) Inventor: Victoria V. Lunyak, Novato, CA (US)

(73) Assignee: Buck Institute for Research on Aging, Novato, CA (US)

( * ) Notice: Subject to any disclaimer, the term of this patent is extended or adjusted under 35 U.S.C. 154(b) by 0 days.

(21) Appl. No.: 13/593,265

(22) Filed: Aug. 23, 2012

(65) Prior Publication Data
US 2013/0065254 A1    Mar. 14, 2013

Related U.S. Application Data

(60) Provisional application No. 61/526,664, filed on Aug. 23, 2011.

(51) Int. Cl.
*C07K 16/18* (2006.01)
*C07K 16/44* (2006.01)
*G01N 33/68* (2006.01)

(52) U.S. Cl.
CPC ............ *C07K 16/18* (2013.01); *G01N 33/6875* (2013.01); *C07K 16/44* (2013.01); *G01N 2440/12* (2013.01); *G01N 2500/00* (2013.01); *G01N 2800/52* (2013.01); *G01N 2800/7042* (2013.01); *C07K 2317/34* (2013.01)
USPC .................. 530/388.85; 530/387.9; 530/391.1

(58) Field of Classification Search
CPC .... C07K 16/18; C07K 16/44; C07K 2317/34; G01N 2440/12; G01N 2800/7042; G01N 33/6875
See application file for complete search history.

(56) References Cited

U.S. PATENT DOCUMENTS

2007/0065890 A1* 3/2007 Reinberg et al. ............. 435/7.23

OTHER PUBLICATIONS

Dousson et al., Eur J Immunol 1989; 19:1123-29.*
Liang et al., Proteome Sci 2008; 6:2, pp. 1-8.*
Wayaku et al., Rheumatol Int 2007; 28:113-9.*
Weiss et al., Epigenetics Chromatin 2010; 3:7, pp. 1-13.*
Tourloupi et al., Clin Exp Immunol. 2005; 142:172-79.*
Lu et al. 2009; 8:4207-15.*
Wisniewski et al., Mol Cell Proteomics, 2007; 6:72-87.*
Berger (2002) "Histone modifications in transcriptional regulation." *Curr Opin Genet Dev* 12: 142-148.
Cook et al. (2009) "Tyrosine dephosphorylation of H2AX modulates apoptosis and survival decisions." *Nature* 458: 591-596; NIH Public Access Author Manuscript pp. 1-16.
Dominguez et al. (1992) "Histone H1 subtype synthesis in neurons and neuroblasts" *Development* 115: 181-185.
Dutnall (2003) "Cracking the histone code: one, two, three methyls, you're out!" *Molecular cell* 12: 3-4.
Feser et al. (2010) "Elevated histone expression promotes life span extension." *Molecular cell* 39(5): 724-735.
Gjerset et al. (1982) "Developmental and hormonal regulation of protein H1 degrees in rodents." *Proc. Natl. Acad. Sci. USA* 79: 2333-2337.
Greer et al. (2010) "Members of the H3K4 trimethylation complex regulate lifespan in a germlinedependent manner in C. elegans." *Nature* 466: 383-387.
Jenuwein et al. (2001) "Translating the Histone Code" *Science* 293: 1074-1080.
Ju et al. (2006) "A Topoisomerase IIβ-Mediated dsDNA Break Required for Regulated Transcription" *Science* 312(5781): 1798-1802.
Katz et al. (2009) "A C. elegans LSD1 demethylase contributes to germline immortality by reprogramming epigenetic memory." *Cell* 137(2): 308-320.
Li et al. (2006) "Nutrient regulates Tor1 nuclear localization and association with rDNA promoter." *Nature* 442: 1058-1061.
Lunyak et al. (2008) "Epigenetic regulation of stem cell fate" *Hum. Mol. Genet.* 17(1): R28-36.
McCormick et al. (2010) "Old yeast can't handle the noise." *Molecular cell* 39: 659-661.
Nielsen et al. (2001) "Heterochromatin formation in mammalian cells: interaction between histones and HP1 proteins." *Molecular Cell* 7: 729-739.
Pina et al. (1987) "Changes in the proportions of histone H1° subtypes in brain cortical neurons" *FEBS Lett.* 210(2): 161-164.
Rando (2012) "Combinatorial complexity in chromatin structure and function: revisiting the histone code." *Curr Opin Genet Dev* 22: 148-155.
Rosenfeld et al. (2006) "Sensors and signals: a coactivator/corepressor/epigenetic code for integrating signal-dependent programs of transcriptional response." *Genes & development* 20: 1405-1428.
Sedelnikova et al. (2004) "Senescing human cells and ageing mice accumulate DNA lesions with unrepairable double-strand breaks" *Nat. Cell Biol.* 6: 168-170.
Simpson (1978) "Structure of the chromatosome, a chromatin particle containing 160 base pairs of DNA and all the histones" *Biochemistry* 17: 5524-5531.
Syed et al. (2010) "Single-base resolution mapping of H1—nucleosome interactions and 3D organization of the nucleosome" *Proc. Natl. Acad. Sci. USA* 107(21): 9620-9625.
Tanaka et al. (2006) "Extent of constitutive histone H2AX phosphorylation on Ser-139 varies in cells with different TP53 status" *Cell Prolif.* 39: 313-323.
Thoma et al. (1979) "Involvement of histone H1 in the organization of the nucleosome and of the salt-dependent superstructures of chromatin" *J. Cell Biol.* 83(2): 403-427.

(Continued)

*Primary Examiner* — Sheela J Huff
*Assistant Examiner* — Jessica H Roark
(74) *Attorney, Agent, or Firm* — Tom Hunter; Weaver Austin Villeneuve & Sampson LLP

(57) ABSTRACT

This invention pertains to markers of cellular senescence. In particular methylation of histone H1 (or isoforms thereof) at residue 172 and/or at residue 180 is a marker of cellular senescence. Antibodies specific to histone H1 (or isoforms thereof) methylated at residue 172 and/or at residue 180 are provided.

16 Claims, 9 Drawing Sheets

(56) References Cited

OTHER PUBLICATIONS

Tollervey et al. (2011) "Merging Innovations to Advance Stem Cell Research and Therapies" *Cell Cycle* 10(24): 4173-4176.
Tollervey et al. (2012) "Epigenetic: judge, jury and executioner of stem cell fate." *Epigenetic* 7(8): 823-840.
Tsang et al. (2003) "Chromatin-mediated regulation of nucleolar structure and RNA Pol I localization by TOR." *The EMBO Journal* 22: 6045-6056.
Tsang et al. (2007) "Compacting DNA during the interphase: condensin maintains rDNA integrity." *Cell Cycle* 6: 2213-2218.
Tsang et al. (2007) "Nutrient starvation promotes condensin loading to maintain rDNA stability." *The EMBO Journal* 26: 448-458.
van Attikum et al. (2005) "The histone code at DNA breaks: a guide to repair?" *Nat. Rev. Mol. Cell Biol.* 6: 757-765.
Vaquero et al. (2009) "Calorie restriction and the exercise of chromatin." *Genes &development* 23(16): 1849-1869.
Vijg et al. (2008) "Puzzles, promises and a cure for ageing." *Nature* 454: 1065-1071.
Wang et al. (2011) "Inhibition of activated pericentromeric SINE/Alu repeat transcription in senescent human adult stem cells reinstates self-renewal" *Cell Cycle* 10(17): 3016-3030.
Wolffe (1989) "Dominant and specific repression of Xenopus oocyte 5S RNA genes and satellite I DNA by histone H1." *EMBO J.*, 8: 527-537.
Wolffe et al. (2000) "Review: chromatin structural features and targets that regulate transcription." *J. Struct. Biol.*, 129(2-3): 102-122.
Xiao et al. (2009) "WSTF regulates the H2A.X DNA damage response via a novel tyrosine kinase activity." *Nature* 457: 57-62.
Zhang et al. (2012) "Reduction of Hox gene expression by histone H1 depletion." *PLoS One* 7: e38829(1-10).
Zoncu et al. (2011) "mTOR: from growth signal integration to cancer, diabetes and ageing." *Nat Rev Mol Cell Biol* 12(1): 21-35.

* cited by examiner

SEQUENCE LISTING

<160> NUMBER OF SEQ ID NOS: 8

<210> SEQ ID NO 1
<211> LENGTH: 19
<212> TYPE: PRT
<213> ORGANISM: Artificial
<220> FEATURE:
<223> OTHER INFORMATION: Histone H1 fragment
<220> FEATURE:
<221> NAME/KEY: misc_feature
<222> LOCATION: (17)..(17)
<223> OTHER INFORMATION: Methylated lysine

<400> SEQUENCE: 1

Ala Lys Pro Val Lys Ala Ser Lys Pro Lys Lys Ala Lys Pro Val Lys
1               5                   10                  15

Xaa Lys Cys

<210> SEQ ID NO 2
<211> LENGTH: 19
<212> TYPE: PRT
<213> ORGANISM: Artificial
<220> FEATURE:
<223> OTHER INFORMATION: Histone H1 fragment
<220> FEATURE:
<221> NAME/KEY: misc_feature
<222> LOCATION: (9)..(9)
<223> OTHER INFORMATION: Methylated lysine

<400> SEQUENCE: 2

Ala Lys Pro Val Lys Ala Ser Lys Xaa Lys Lys Ala Lys Pro Val Lys
1               5                   10                  15

Pro Lys Cys

<210> SEQ ID NO 3
<211> LENGTH: 19
<212> TYPE: PRT
<213> ORGANISM: Artificial
<220> FEATURE:
<223> OTHER INFORMATION: Histone H1 fragment
<220> FEATURE:
<221> NAME/KEY: misc_feature
<222> LOCATION: (9)..(9)
<223> OTHER INFORMATION: Methylated lysine
<220> FEATURE:
<221> NAME/KEY: misc_feature
<222> LOCATION: (17)..(17)
<223> OTHER INFORMATION: Methylated lysine

<400> SEQUENCE: 3

Ala Lys Pro Val Lys Ala Ser Lys Xaa Lys Lys Ala Lys Pro Val Lys
1               5                   10                  15

Xaa Lys Cys

<210> SEQ ID NO 4
<211> LENGTH: 13
<212> TYPE: PRT
<213> ORGANISM: artificial
<220> FEATURE:
<223> OTHER INFORMATION: Modified histone H1 fragment
<220> FEATURE:
<221> NAME/KEY: MOD_RES
<222> LOCATION: (1)..(1)
<223> OTHER INFORMATION: Acetylated threonine
<220> FEATURE:
<221> NAME/KEY: MOD_RES
<222> LOCATION: (5)..(5)
<223> OTHER INFORMATION: Acetylated lysine
<220> FEATURE:

```
<221> NAME/KEY: MOD_RES
<222> LOCATION: (8)..(8)
<223> OTHER INFORMATION: Protonated lysine
<220> FEATURE:
<221> NAME/KEY: MOD_RES
<222> LOCATION: (10)..(10)
<223> OTHER INFORMATION: Phosphorylated serine

<400> SEQUENCE: 4

Xaa Val Lys Ala Xaa Pro Val Xaa Ala Xaa Lys Pro Lys
 1               5                  10

<210> SEQ ID NO 5
<211> LENGTH: 13
<212> TYPE: PRT
<213> ORGANISM: Artificial
<220> FEATURE:
<223> OTHER INFORMATION: Modified histone H1 fragment
<220> FEATURE:
<221> NAME/KEY: MOD_RES
<222> LOCATION: (2)..(2)
<223> OTHER INFORMATION: Phosphorylated serine
<220> FEATURE:
<221> NAME/KEY: MOD_RES
<222> LOCATION: (3)..(3)
<223> OTHER INFORMATION: Methylated lysine
<220> FEATURE:
<221> NAME/KEY: MOD_RES
<222> LOCATION: (11)..(11)
<223> OTHER INFORMATION: Methylated lysine
<220> FEATURE:
<221> NAME/KEY: MOD_RES
<222> LOCATION: (13)..(13)
<223> OTHER INFORMATION: Protonated lysine

<400> SEQUENCE: 5

Ala Xaa Xaa Pro Lys Lys Ala Lys Pro Val Xaa Pro Xaa
 1               5                  10

<210> SEQ ID NO 6
<211> LENGTH: 15
<212> TYPE: PRT
<213> ORGANISM: Artificial
<220> FEATURE:
<223> OTHER INFORMATION: Peptide linker

<400> SEQUENCE: 6

Gly Gly Gly Gly Ser Gly Gly Gly Gly Ser Gly Gly Gly Gly Ser
 1               5                  10                  15

<210> SEQ ID NO 7
<211> LENGTH: 5
<212> TYPE: PRT
<213> ORGANISM: Artificial
<220> FEATURE:
<223> OTHER INFORMATION: Peptide linker

<400> SEQUENCE: 7

Ser Ser Ser Ser Gly
 1               5

<210> SEQ ID NO 8
<211> LENGTH: 15
<212> TYPE: PRT
<213> ORGANISM: Artificial
<220> FEATURE:
<223> OTHER INFORMATION: Peptide linker
```

```
<400> SEQUENCE: 8

Ser Ser Ser Ser Gly Ser Ser Ser Ser Gly Ser Ser Ser Gly
1               5                   10                  15
```

EPIGENETIC MECHANISMS RELATED TO DNA DAMAGE AND AGING

CROSS-REFERENCE TO RELATED APPLICATIONS

This application claims benefit of and priority to U.S. Ser. No. 61/526,664, filed on Aug. 23, 2011, which is incorporated herein by reference in its entirety for all purposes.

STATEMENT OF GOVERNMENTAL SUPPORT

[Not Applicable]

BACKGROUND

Packaging of chromatin is modified by the cell in a myriad of different ways, most profoundly through either a complete loss of histones from DNA or the establishment of (in simplistic terms) a different degree of chromatin condensation through the complex, combinatorial code of histone post-translational modifications (PTMs). These modifications are designated either to tighten or loosen chromatin in order to modulate access to the DNA sequence. This modulation influences major biological processes within the cells such as gene transcription, faithful genome duplication in dividing cells and DNA repair (Lunyak and Rosenfeld (2008) *Hum Mol. Genet.*, 17: R28-36; Jenuwein and Allis (2001) *Science* 293: 1074-1080). The recent identification of enzyme systems carrying out histone modifications, together with the discovery of binding proteins that "read" PTMs on histones, has led to the proposal that the pattern of modifications acts as an information code that influences gene transcription, DNA repair, genome integrity and nuclear architecture. Evidence suggests that once a code is generated, it can serve as an independent signal that allows the recruitment of a downstream regulatory protein(s) (Lunyak and Rosenfeld (2008) *Hum Mol. Genet.*, 17: R28-36; Jenuwein and Allis (2001) *Science* 293: 1074-1080; Rosenfeld et al. (2006) *Genes Dev.*, 20: 1405-1428).

Current research links cellular and tissue aging to changes in chromatin structure in a variety of model systems. It has been shown that normal aging is accompanied by a profound loss of histone proteins from the genome (Feser et al. (2010) *Mol Cell* 39: 724-735). Excitingly, lifespan can be extended by manipulations that reverse these age-dependent changes in chromatin structure, indicating a pivotal role for chromatin dynamics in aging (Feser et al. (2010) *Mol. Cell.* 39: 724-735; McCormick and Kennedy (2010) *Mol. Cell.* 39: 659-661). Examples include, but are not limited to, the findings that a complete or partial knockdown of enzymes responsible for histone H3 lysine ($^{me}K_9$ and $^{me}K_4$) demethylation/methylation results in life extension (Katz et al. (2009) *Cell* 137: 308-320; Greer et al. (2010) *Nature* 466: 383-387), and that phosphorylation at serine 139 ($^{ph}S_{139}$), known as γH2AX (Tanaka et al. (2006) *Cell Prolif.*, 39: 313-323), is a critical component of DNA damage response (DDR) and cellular senescence (Sedelnikova et al. (2004) *Nat. Cell Biol.*, 6: 168-170).

Aging cells, confronted with DNA-damage resulting from a variety of stimuli under normal, physiological conditions, make fundamental decisions either to repair DNA or trigger an apoptotic or senescence response (Vijg and Campisi (2008) *Nature* 454: 1065-1071; Xiao et al. (2009) *Nature* 457: 57-62; Cook et al. (2009) *Nature* 458, 591-596). Post translational modifications (PTMs) of H2AX serve as a component of the adjudication between these outcomes. In the DNA repair pathways, some chromatin modifications seem to play a critical role in marking lesions or recruiting factors involved in repair, thus facilitating the function of repair proteins. The best characterized in this context are histone H2AX and H1 phosphorylation events (van Attikum and Gasser (2005) *Nat. Rev. Mol. Cell. Biol.* 6: 757-765; Ju et al. (2006) *Science* 312: 1798-1802). It is believed however, that the full spectrum of histone PTMs relevant to aging of adult stem and somatic cells and their combinatorial patterns specific for the molecular pathways that limit longevity are unknown.

The H1 histone class proteins function at several levels of chromatin organization: it binds at the entry/exit sites of the nucleosomal core DNA to seal of the DNA wrapping at the histone octamer surface (Simpson (1978) *Biochemistry* 17: 5524-5531) and are a prerequisite for the formation of the next level of chromatin organization in forming 30 nm fibers of supranucleosomal chromatin (Wolffe 91989) *EMBO J.*, 8: 527-537; Thoma et al. (1979) *J. Cell Biol.*, 83: 403-427). Evidence indicates that histone H1 class proteins influence the accessibility of the chromosomal DNA upon DNA replication, gene transcription and repair (Ju et al. (2006) *Science*, 312: 1798-1802; Wolffe et al. (2000) *J. Struct. Biol.*, 129: 102-122; Syed et al. (2010) *Proc. Natl. Acad. Sci. USA*, 107: 9620-9625; Nielsen et al. (2001) *Molecular Cell*, 7: 729-739; Zhang et al. (2012) *PLoS One* 7: e38829). The existence of several non-allelic variants of the H1 histone may thus provide a means to modulate the contributions of the H1 histones to supranucleosomal chromatin$_{37}$,$^{38}$ as well as preserve genome integrity (Vujatovic et al. (2012) *Nucleic Acids Res.*, 40: 5402-5414). Histone H1.0 has been described in several mammalian species (Panyim and Chalkley 91969) *Biochem. Biophys. Res. ommun.*, 37: 1042-1049) and Gjerset et al. (1982) *Proc. Natl. Acad. Sci. USA*, 79: 2333-2337, have demonstrated that the synthesis of H1.0 in rodents is developmentally and hormonally controlled. Since H1.0 replaces main type of H1 histones upon chromatin remodeling, it is frequently referred to as a replacement histone variant (Doenecke and Alonso 91996) *Int. J. Dev. Biol.*, 40: 395-401). H1.0 in vivo is confined to highly differentiated cells in several cell systems but its changing pattern during development and dependence on hormonal stimuli suggests that H1.0 also plays a role upon development and differentiation (Pina and Suau (1987) *FEBS Lett.*, 210: 161-164; Dominguez et al. (1992) *Development* 115: 181-185; Julien et al. (2010) *Proc. Natl. Acad. Sci. USA*, 107: 5483-5488). Interestingly, It has been demonstrated that progesterone receptor (PR) regulated chromatin changes are required a cooperative action of ATP-dependent remodeling, histone methylatrasferases (HMTs), and kinase activation for generic H1 displacement and is a prerequisite for the subsequent displacement of histone H2A/H2B catalyzed by PCAF and BAF (Vicent et al. (2011) *Genes & Development* 25: 845-862), thus suggesting that cascades of the epigenomic regulations may converge on this family of histones.

SUMMARY

Cellular chromatin is a dynamic polymer, capable of many configurations and prone to remodeling and restructuring as it receives physiologically relevant input from development-specific, cell-type specific or environmental signaling pathways. Differential chromatin condensation achieved by histone posttranslational modifications (PTMs) underlies packaging of chromatin (Lunyak and Rosenfeld 92008) *Hum. Mol. Genet.*, 17: R28-36; Jenuwein and Allis (2001) *Science*, 293: 1074-1080). Undoubtedly, histone PTMs (epigenetic code) play critical roles in many aspects of the cellular responses tightly linked to organismal development, human disease and aging. By applying novel analytical proteomic technology previously unreported meK172-meK180 modifications of H1.0 associated with ex-vivo aging of human adult stem cells were identified. Histone H1.0 is retinoid acid inducible histone replacement variant previously linked to chromatin organization in adult and developing tissues (Pina and Suau (1987) *FEBS Lett.*, 210: 161-164; Dominguez et al. (1992) *Development* 115: 181-185; Gjerset et al. (1982) *Proc. Natl. Acad. Sci. USA*, 79: 2333-2337). Novel antibodies specific to these PTMs were successfully created.

Accordingly, in certain embodiments the methods and compositions described herein pertain to the discovery of specific histone (H1 (H1.0)) post-translational modifications (e.g., methylation at residue 172 and/or 180) that correlate with cellular senescence. In certain embodiments methylation of histone H1 (H1.0) at one or both sites is a biomarker of cell fitness and/or a biomarker of success upon chemotherapy in cancer treatment, and/or a marker of DNA damage (e.g., in coincidence with γH2AX deposition), and/or an indicator of replicative and genotoxic stress-induced senescence (e.g., a biomarker of the aging process and/or cellular fitness).

In various embodiments, antibodies are provided that that specifically binds to these markers and the use of these antibodies in a number of methods including, but not limited to methods of monitoring a chemotherapeutic regimen. Antibodies against these novel PTMs are directly or indirectly modulated by cellular TOR pathway and can be used in the reporter assays for siRNA, small molecules, organic or synthetic compound screening to identify active compounds for drug development.

In certain embodiments an antibody is provided that specifically binds a methylated histone H1 or a methylated histone H1 isoform where the methylated histone H1 comprises one or more methyl group(s) on H1 residue 172, one or more methyl groups on H1 residue 180, or one or more methyl groups on H1 residues 182, or one or more methyl groups on a residue corresponding to H1 residue 172, 180, or both residues, the H1 residues being numbered according to human H1. In certain embodiments the H1 residue 172 is mono-, di-, or trimethylated K (lysine). In certain embodiments the H1 residue 180 is mono-, di-, or trimethylated K (lysine). In certain embodiments the antibody specifically binds one or more peptides selected from the group consisting of AKPVKASKPKKAKPVKmePKC (SEQ ID NO:1), AKPVKASKmePKKAKPVKPKC (SEQ ID NO: 2), and AKPVKASKmePKKAKPVKmePKC (SEQ ID NO:3). In certain embodiments the antibody comprises a polyclonal antibody. In certain embodiments the antibody comprises a monoclonal antibody. In certain embodiments the antibody comprises an IgG or an IgA, or an IgM. In certain embodiments the antibody comprises a Fab or a (Fab')$_2$. In certain embodiments the antibody comprises a single chain Fv (scFv). In certain embodiments the antibody comprises a (scFv')$_2$. In certain embodiments the antibody binds (e.g., specifically binds 0 to a translationally modified mammalian H1 histone. In certain embodiments the antibody binds to a human metH1. In various embodiments the antibody is attached to a detectable label (e.g., a spin label, a colorimetric label, a radioactive label, an enzymatic label, a fluorescent label, a magnetic label, and the like).

In certain embodiments methods are provided for detecting a post translational modification of a H1 histone in a sample (e.g., a biological sample). In certain embodiments the methods comprise contacting the sample, or a derivative of the sample with an antibody described herein that specifically binds a methylated histone H1 or a methylated histone H1 isoform where the methylated histone H1 comprises one or more methyl group(s) on H1 residue 172, one or more methyl groups on H1 residue 180, or one or more methyl groups on H1 residues 182, or one or more methyl groups on a residue corresponding to H1 residue 172, 180, or both residues, the H1 residues being numbered according to human H1; and detecting the signal, where association of the signal with a histone or histone fragment in (or from) the sample indicates the presence and/or amount of histone H1, or a histone H1 isoform, methylated at residue 172 (or the isoform residue corresponding to H1 172) and/or at residue 180 (or the isoform residue corresponding to H1 180). In certain embodiments the label is attached to the antibody. In certain embodiments the label is attached to a ligand that binds to the antibody. In certain embodiments the second ligand is a second antibody. In certain embodiments the label is selected from the group consisting of a colorimetric label, a chemiluminescent label, a fluorescent label, an electrochemical label, a magnetic label, and combinations thereof. In certain embodiments the label comprises a fluorescent dye. In various embodiments the method is performed in a high throughput (HTS) format. In certain embodiments the sample comprises, or is derived from, cells of a non-human mammal. In certain embodiments the sample comprises, or is derived from, human cells. In certain embodiments the cells comprise ADSCs.

In certain embodiments a method of monitoring and selecting a chemotherapeutic regimen in a subject, is provided where the method comprises detecting and/or quantifying cells with histone H1 methylated at residue 172 and/or at histone H1 residue 180, and/or an H1 isoform having methylated residue(s) corresponding to H1 172 and/or 180, in a biological sample derived from the subject detect; and increasing the chemotherapeutic dosage regimen to a level where cancer cells comprising said sample show histone H1 methylated at residue 172 and/or at residue 180, or H1 isoform residue(s) corresponding to H1 172 and/or 180 are methylated. In certain embodiments the method comprises detecting cytoplasmic deposition of the methylated histone(s). Also provided of a method of monitoring and selecting a chemotherapeutic regimen in a subject, where the method comprises detecting and/or quantifying cells histone H1 methylated at residue 172 and/or at histone H1 residue 180, and/or an H1 isoform with methylated residue(s) corresponding to H1 172 and/or 180, in a biological sample derived from the subject; and decreasing the chemotherapeutic dosage regimen where normal (non-cancer cells) show little or no cytoplasmic deposition of histone H1 methylated at residue 172 and/or at residue 180, and/or said hl isoform shows little or no methylation at residue(s) corresponding to H1 172 and/or 180. In certain embodiments the method comprises detecting cytoplasmic deposition of the methylated histone(s). Also provided is a method of monitoring the efficiency of senescence induction in cancer cells in a subject at a given chemotherapeutic dosage regimen, where the method typically comprises detecting and/or quantifying histone H1 methylated at residue 172 and/or at residue 180, or an H1 isoform methylated at residue(s) corresponding to H1172 and/or 180, in a biological sample comprising cancer cells derived from the subject where the ratio of cells (e.g., cancer cells) showing the methylation compared to cells not showing such methylation provides a measure of the efficiency of senescence induction at that dosage regimen. In certain embodiments the method further comprises adjusting the chemotherapeutic dosage to so that at least about 10% of the cancer cells show the methylation. In various embodiments of these methods the dosage regimen is adjusted so that the occurrence of histone H1 methylated at residue 172 and/or at histone H1 residue 180 ranges from about 10% to about 70% of the sample. In certain embodiments the cancer is a leukemia or a lymphoma. In certain embodiments the cancer is a solid tumor. In certain embodiments the cancer is a metastatic cancer. In certain embodiments the cancer is a stage III, stage IV, or stage V cancer. In certain embodiments the cancer is selected from the group consisting of breast cancer, gastric cancer, bladder cancer, ovarian cancer, thyroid cancer, lung cancer, prostate cancer, uterine cancer, testicular cancer, neuroblastoma, glioblastoma, squamous cell carcinoma of the head, neck, cervix and vagina, multiple myeloma, lymphoma, leukemia, and soft tissue and osteogenic sarcoma. In certain embodiments the sample comprises a sample selected from the group consisting of blood, lymph, serum, cerebrospinal fluid, urine, tracheal lavage, buccal scrape, tissue biopsy, and needle biopsy. In certain embodiments the sample comprises a tissue biopsy. In certain embodiments the sample comprises tissue suspected of being cancerous. In certain embodiments the biological sample is from a non-human mammal. In certain embodiments the biological sample is from a human. In certain embodiments the methylation is detected using a method selected from the group consisting of an immunoassay, flow cytometry, mass-spectrometry, NMR, and microfluidics. In certain embodiments the methylation is determined using an immunoassay (e.g., an immunoassay utilizing one or more of the antibodies described herein). In certain embodiments the immunoassay comprises an ELISA or a Western Blot. In certain embodiments the immunoassay is selected from the group consisting of ELISA, a lateral flow immunoassay, a magnetic immunoassay, a radioimmunoassay, immunoassay coupled mass-spectrometry, quantitative mass-spectrometry, and a surround Optical Fiber Immunoassay (SOFIA).

In certain embodiments methods of quantifying DNA damage in a cell or tissue are provided where the methods comprise detecting and/or quantifying histone H1 methylated at residue 172 and/or at residue 180 (or an H1 isoform residue corresponding to H1 172 and/or 180) in a biological sample comprising the cell or tissue, where histone H1 methylated at residue 172 and/or at residue 180 (or the isoform residue corresponding to H1 172 and/or 180) is a surrogate marker for DNA damage in the cell or tissue. Methods of quantifying replicative and/or genotoxic stress-induced senescence of mammalian cells are also provided where the methods comprise detecting and/or quantifying histone H1 or histone H1 isoform methylated at residue 172 and/or residue 180, or the isoform residue corresponding to H1 172 and/or the isoform residue corresponding to H1 180, in a biological sample comprising the cell or tissue, where methylation of histone H1 at residue 172 and/or at histone H1 residue 180, and/or methylation of the H1 isoform at residues corresponding to H1 residue 172 and/or 180 is a marker replicative and/or genotoxic stress-induced senescence of the cell(s). In certain embodiments the amount of cells methylated and/or the degree of methylation is proportional to the magnitude of replicative and/or genotoxic stress-induced senescence of the cell(s).

In various embodiments screening systems are also provided. One illustrative screening system provides a method of identifying compounds that have anti-aging activity, where the method comprises contacting test cells with one or more test agents; and detecting and/or quantifying methylation of histone H1 or histone H1 isoform methylated at residue 172 and/or at residue 180 (or the isoform residue corresponding to H1 172 and/or 180) in the cells; and scoring test agents that reduce histone H1 or H1 isoform methylation at residue 172 and/or at residue 180, or the isoform residue corresponding to H1 172 and/or 180, in the cells as compared to control cells as candidate compounds that have anti-aging activity. In certain embodiments the test cells and the control cells are contacted with one or more agents that typically induce senescence. In certain embodiments the control cells are cells exposed to the test agent(s) at a lower concentration than the test cells. In certain embodiments the control cells are cells that are not exposed to the test agent(s). In certain embodiments the contacting comprises contacting the test agent(s) to the cells in vitro. In certain embodiments the method is performed in a high throughput screening (HTS) format. In certain embodiments the contacting comprises administering the test agent to a non-human mammal. In certain embodiments the methylation is detected and/or quantified using a method selected from the group consisting of an immunoassay, flow cytometry, mass-spectrometry, NMR, and microfluidics. In certain embodiments the methylation is determined using an immunoassay (e.g., utilizing one or more antibodies described herein). In certain embodiments the immunoassay comprises an ELISA or a Western Blot. In certain embodiments the immunoassay is selected from the group consisting of ELISA, a lateral flow immunoassay, a magnetic immunoassay, a radioimmunoassay, and a surround Optical Fiber Immunoassay (SOFIA).

Also provided are diagnostic kits for determining the level of histone H1 methylation (or methylation of an H1 isoform). In certain embodiments the kits comprise a container containing a first antibody that specifically binds to a methylated H1 histone (preferably to an H1 histone methylated at residue 172 and/or at residue 180) as described herein; and optionally a secondary antibody directed against the first antibody; optionally a secondary antibody directed against said first antibody; and optionally reagents for the measurement of a signal derived from an antibody binding to methylated H1 histone. In certain embodiments the kit comprises a secondary antibody directed against the first antibody. In certain embodiments the kit comprises reagents for the measurement of a signal derived from an antibody binding to methylated H1 histone. In certain embodiments the kit further comprises instructional materials providing protocols for the use of the kit to detect methylation of an H1 histone.

Also provided are methods of producing the antibodies that specifically bind to a methylated H1 histone (preferably to an H1 histone methylated at residue 172 and/or at residue 180) as described herein, where the methods comprise administering a histone H1, or a fragment thereof, to a mammal, where the H1 or H1 fragment comprises methylated H1 residue 172, or methylated H1 residue 180, or both methylated H1 residue 172 and methylated H1 residue H180, the H1 residues being numbered according to human H1, and where the administration elicits an immune response; and recovering an antiserum or spleen cells from the mammal. In certain embodiments the spleen cells are recovered and used to produce one or more hybridomas. In certain embodiments the histone H1 fragment comprises a peptide selected from the group consisting of AKPVKASKPKKAKPVKmePKC (SEQ ID NO:1), AKPVKASKmePKKAKPVKPKC (SEQ ID NO: 2), and AKPVKASKmePKKAKPVKmePKC (SEQ ID NO:3).

DEFINITIONS

As used herein, the term "biological sample" refers to any physiological material containing histone H1 (or H1.0 variant). A biological sample will generally also typically include chromatin, often chromatin comprising one or more genes coding protein(s), no-coding RNA or genomic repeated sequences. A biological sample can be obtained, for example, from cell culture, primary cells isolated directly from an organism, histological samples, biopsy and may be subjected to any desired processing steps, e.g., concentration or dilution.

As used with respect to polypeptides or polynucleotides, the term "isolated" refers to a polypeptide or polynucleotide that has been separated from at least one other component that is typically present with the polypeptide or polynucleotide. Thus, a naturally occurring polypeptide is isolated if it has been purified away from at least one other component that occurs naturally with the polypeptide or polynucleotide. A recombinant polypeptide or polynucleotide is isolated if it has been purified away from at least one other component present when the polypeptide or polynucleotide is produced.

The terms "peptide", "polypeptide" and "protein" are used interchangeably herein to refer a polymer of amino acids, and unless otherwise specified, include atypical amino acids that can function in a similar manner to naturally occurring amino acids.

The terms "amino acid" or "amino acid residue," include naturally occurring L-amino acids or residues, unless otherwise specifically indicated. The commonly used one- and three-letter abbreviations for amino acids are used herein (Lehninger (1975) Biochemistry, 2d ed., pp. 71-92, Worth Publishers, N.Y.). The terms "amino acid" and "amino acid residue" include D-amino acids as well as chemically modified amino acids, such as amino acid analogs, naturally occurring amino acids that are not usually incorporated into proteins, and chemically synthesized compounds having the characteristic properties of amino acids (collectively, "atypical" amino acids). For example, analogs or mimetics of phenylalanine or proline, which allow the same conformational restriction of the peptide compounds as natural Phe or Pro are included within the definition of "amino acid."

Illustrative atypical amino acids include, for example, those described in International Publication No. WO 90/01940 as well as 2-amino adipic acid (Aad) which can be substituted for Glu and Asp; 2-aminopimelic acid (Apm), for Glu and Asp; 2-aminobutyric acid (Abu), for Met, Leu, and other aliphatic amino acids; 2-aminoheptanoic acid (Ahe), for Met, Leu, and other aliphatic amino acids; 2-aminoisobutyric acid (Aib), for Gly; cyclohexylalanine (Cha), for Val, Leu, and Ile; homoarginine (Har), for Arg and Lys; 2,3-diaminopropionic acid (Dpr), for Lys, Arg, and H is; N-ethylglycine (EtGly) for Gly, Pro, and Ala; N-ethylasparagine (EtAsn), for Asn and Gln; hydroxyllysine (Hyl), for Lys; allohydroxyllysine (Ahyl), for Lys; 3- (and 4-) hydroxyproline (3Hyp, 4Hyp), for Pro, Ser, and Thr; allo-isoleucine (Aile), for Ile, Leu, and Val; amidinophenylalanine, for Ala; N-methylglycine (MeGly, sarcosine), for Gly, Pro, and Ala; N-methylisoleucine (MeIle), for Ile; norvaline (Nva), for Met and other aliphatic amino acids; norleucine (Nle), for Met and other aliphatic amino acids; ornithine (Orn), for Lys, Arg, and H is; citrulline (Cit) and methionine sulfoxide (MSO) for Thr, Asn, and Gln; N-methylphenylalanine (MePhe), trimethylphenylalanine, halo (F, Cl, Br, and I) phenylalanine, and trifluorylphenylalanine, for Phe.

As used with reference to a polypeptide, the term "full-length" refers to a polypeptide having the same length as the mature wild-type polypeptide.

The term "fragment" is used herein with reference to a polypeptide to describe a portion of a larger molecule. Thus, a polypeptide fragment can lack an N-terminal portion of the larger molecule, a C-terminal portion, or both. In certain embodiments the fragment comprises at least 8, or at least 9, or at least 10, or at least 11, or at least 12, or at least 13, or at least 14, or at least 15, or at least 20, or at least 25, or at least 30, or at least 35, or at least 40, or at least 45, or at least 50 contiguous amino acids of the wild type protein.

As used with reference to polypeptides, the term "wild-type" refers to any polypeptide having an amino acid sequence present in a polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized.

A "histone H1 isoform" refers to a member of the histone H1 family. The H1 family of linker histones is the most divergent class of histone proteins. As of 2009, genes coding for eleven different H1 subtypes have been identified in the human genome. This family of histones can be subdivided according to different criteria. A useful way to describe different histones is the mode of expression of the respective genes. In this way, we may differentiate between histone genes that are expressed in somatic cells during the S phase of the cell cycle and are located within large histone gene clusters (the genes encoding histones H1.1 to H1.5), two histone genes with a variant mode of expression in somatic cells (H1.0 (or H1) and H1x), and finally four H1 histone genes expressed in germ cells, i.e. the testicular isoform genes H1t, H1T2 and HILS1, and the gene encoding the oocytic Hloo (see, e.g., Happel and Doenecke (2009) *Gene* 431: 1-12).

"Methylation at H1 residue K172 and/or K180" indicates that the histone is has one or more methyl groups (e.g., mono-, di-, tri-methylated) attached to the lysine at residue 172 and/or 180 in the H1 (H1.0 histone). Methylation at a residue that corresponds to residue 172 and/or 180 in the H1 (H1.0 histone) indicates that corresponding residues in H1 isoforms (family members) are methylated.

Residues in two or more polypeptides are said to "correspond" if they are either homologous (i.e., occupying similar positions in primary, secondary, or tertiary structure) or analogous (i.e., having the same or similar functional capacities). As is well known in the art, homologous residues can be determined by aligning the polypeptide sequences for maximum correspondence as described above. A multiple alignment of the protein sequences of human H1 histones: H1.1 (Genbank Accession No: NM_005325), H1.2 (Accession No: BC002649), H1.3 (Accession No: NM_005320), H1.4 (Accession No: NM_005321), H1.5 (Accession No: NM_005322), H1.0 (Accession No: NM_005318), H1t (Accession No: NM_005323), H1x (Accession No: BC000426), H1oo (Accession No: NM_153833), H1T2 (Accession No: NM_181788), and H1 histone-like HILS1 (Accession No: AY286318) is provided in Happel and Doenecke (2009) *Gene* 431: 1-12, which is incorporated herein by reference for that multiple sequence alignment.

Residue positions in polypeptides discussed herein are identified with respect to a reference amino acid sequence. Thus, the phrase "histone H1 (H1.0) residues are numbered according to human H1 (H1.0)" indicates that the numbering of the human H1 (H1.0) histone is used to identify residue positions. In this case, a reference to "H1 residue 172" identifies a residue that, in human H1, is the $172^{nd}$ amino acid from the N-terminus. This residue is a lysine (K) in human H1.0. Those of skill in the art appreciate that this residue can have a different position in H1 proteins from different species or in different isoforms and, indeed, can be a different amino acid.

As used herein, an "antibody" refers to a protein consisting of one or more polypeptides substantially encoded by immunoglobulin genes or fragments of immunoglobulin genes.

The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (V-) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region thereby converting the $(Fab')_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term "antibody", as used herein also includes antibody fragments either produced by the modification of whole antibodies or synthesized de novo using recombinant DNA methodologies. In certain embodiments, suitable antibodies include, but are not limited to, single chain antibodies, more preferably single chain Fv (scFv) antibodies in which a variable heavy and a variable light chain are joined together (directly or through a peptide linker) to form a continuous polypeptide.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs." Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface." This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

A single chain Fv ("scFv") antibody is a covalently linked $V_H$::$V_L$ heterodimer that forms a single antigen binding domain. Two scFv chains can be linked, covalently or non-covalently, to form an $(scFv')_2$ antibody, which has two antigen binding domains, which can be the same or different.

As used herein, the term "antibody" includes any antibody conjugated to any other substance, e.g., labeled antibodies, antibodies conjugated to polymeric beads, etc.

As used herein, the terms "antibody binding" and "immunoreactivity" refer to the non-covalent interactions of the type which occur between an immunoglobulin molecule and an antigen for which the immunoglobulin is specific. The strength or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity and is thus equal to the dissociation constant $K_d$ (see, generally, Davies et al. (1990) Ann. Rev. Biochem., 59: 439-473).

The phrase "specifically binds" is used herein with reference to an antibody to describe a binding reaction which is determinative of the presence of the corresponding antigen in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, an anti-H1 $^{me}$K172 and/or $^{me}$K180 antibody preferentially binds to histone H1 methylated as position 172, to histone H1 methylated at residue 180, or to histone H1 methylated at both positions over the H1 form lacking a methyl at residue 172, at residue 180, or at both residues. A variety of immunoassay formats may be used to select antibodies specifically immunoreactive with a particular protein. For example, solid-phase ELISA immunoassays are routinely used to select monoclonal antibodies specifically immunoreactive with a protein (see, e.g., Harlow and Lane (1988) Antibodies, A Laboratory Manual, Cold Spring Harbor Publications, New York, for a description of immunoassay formats and conditions that can be used to determine specific immunoreactivity).

The term "anti-H1 meK172 and/or meK180 antibody" refers to an antibody that specifically binds to an H1 histone methylated at residue 172, to an antibody that specifically binds to an H1 histone methylated at residue 180, or to an antibody that specifically binds to an H1 histone methylated at both residues 172 and 180.

A "test agent" is any agent that can be screened in the prescreening or screening assays described herein. The test agent can be any suitable composition, including, but not limited to, a small molecule, peptide, polypeptide, protein, or protein complex.

BRIEF DESCRIPTION OF THE DRAWINGS

FIG. 2A shows a dot blot hybridization with synthetic peptide $^{me}$K172H1. FIG. 2B shows a dot blot hybridization with synthetic peptide $^{me}$K172$^{me}$K180H1. FIG. 2C shows a Western Blot hybridization of chromatin extracts from adult stem cells with lysine methylation specific antibodies against H1.

FIG. 4A: Cells we treated with 50 µg/ml bleomycin for 3 hrs. Drug was replaced with normal DMEM12 media and cells were assessed for $^{me}$K172$^{me}$K180 histone H1 methylation and DNA damage γH2AX at different time points (panels A, B, and C) by immunohistochemistry. Cellular senescence was estimated by senescence-associated β-Gal activity (phase-contrast). FIGS. 4B and 4C show the results of Western blots using H1.0 methyl antibodies in crude cellular extracts from human ADSCs treated with Rapamycin (FIG. 4B) or rampamyucin and bleomycin (FIG. 4C). TOR pathway suppression by rapamycin results in decrease of H1.0 methylation upon genotoxic-stress induces senescence and acute DDR. No changes on H1.0 expression after rapamycin treatment were observed in self-renewing or senescent hADSCs. However, acute DDR results in transcriptional up regulation of H1.0 gene expression that could be influenced by TOR pathway suppression. 1, 2, 3—represent samples of three independent hADSCs cultures used in western blot and qPCR experiments.

DETAILED DESCRIPTION

Figure 1:
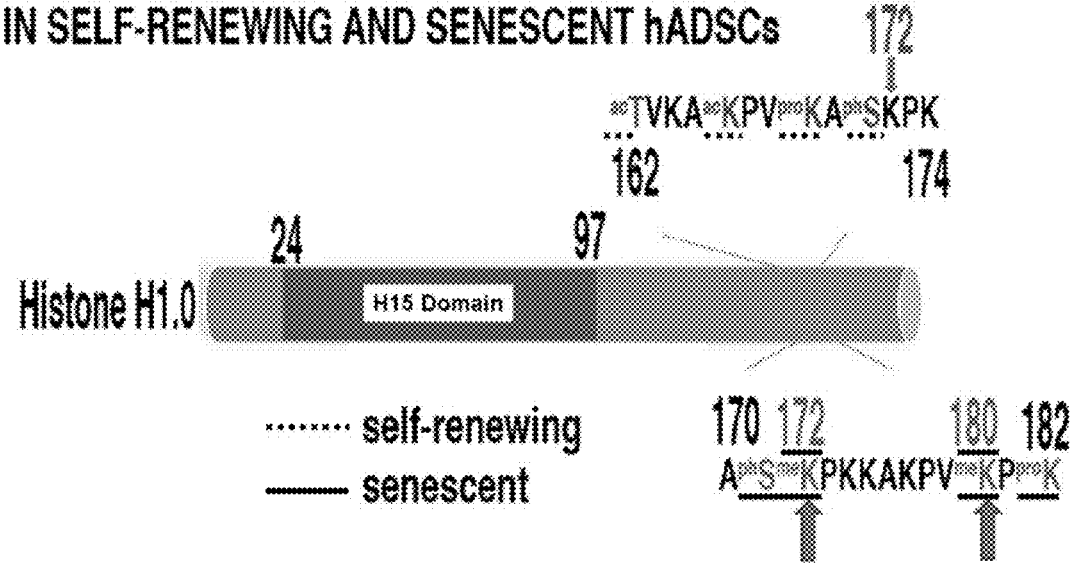
FIG. 1 schematically illustrates an example of H1.0 modifications and peptide sequences. Histone H1.0: residues 162-174 (SEQ ID NO:4), residues 170-182 (SEQ ID NO:5).

In an effort to understand how changes in chromatin structure and function affect aging on cellular and organismal levels the role of chromatin in modulation of the cellular transcriptional programs was investigated to identify, characterize, and understand the function of the aging related histone post-translational modifications (PTMs). Novel and previously unreported aging-associated lysine methylation of histone H1.0 was discovered. In particular, these modifications were identified and data linking these PTMs to DNA damage response pathways and, ultimately, to cellular senescence of adult stem cells or somatic cells were identified. In addition, antibodies suitable for identification of these PTMs were also developed.

More particularly, it was demonstrated that H1.0 methylation is directly linked to the DNA damage response (DDR), which governs genome stability, stem cell self-renewal and cellular secretory phenotypes among many others. In addition, experimental evidence that methylated form of H1.0 is evicted from chromatin under conditions of persistent DDR (senescence) was also obtained. The data presented herein indicate that both replicative and genotoxic stress-induced senescence, as well as acute DNA damage of human stem and somatic cells manifest increase in H1.0 methylation.

Moreover, it was determined that H1.0 PTMs are sensitive to inhibition of the TOR pathway. A preliminary assessment of a key component of TOR pathway (phS6K1 and its downstream target S6) in stem and somatic cells upon genotoxic-stress induced senescence, as well as under acute DDR was performed. The data indicate that TOR suppression correlated with loss of E11.0 methylation, thus establishing more compelling indicating that 1) H1.0 methylation, or/and 2) HTMs and HDMTs which are responsible for changes in K172K180 H1.0 methylation, can be downstream targets of TOR.

Accordingly, in various embodiments compositions and methods are provided for detecting methylation of the H1 histone at residue 172, at residue 180, and/or at both residues 172 and 180. In particular, it is demonstrated that meK172 and/or meK180 methylation of H1.0 occurs upon DNA damage in coincidence with γH2AX deposition, and therefore, methylation of H1 histone at one or both of these sites can be viewed as a marker for DNA damage. Accordingly, in certain embodiments, methods are provided for detecting and/or quantifying DNA damage in a cell or tissue. The method typically involves detecting and/or quantifying methylation of histone H1 at residue 172 and/or at histone H1 residue 180 in a biological sample comprising said cell or tissue, wherein methylation of histone H1 at residue 172 and/or at histone H1 residue 180 is a marker for DNA damage in said cell or tissue.

The eviction of meK172 and/or meK180 methylated form of H1.0 from chromatin and its redistribution to the cytoplasm of senescent adult stem cells (ADSCs) is also demonstrated and this correlates with a decline of H1.0 chromatin representation in the nucleus. These data indicate that both replicative and genotoxic stress-induced senescence of human stem and somatic cells manifest drastic eviction of methylated histone H1.0 from chromatin. Thus these PTMs can be effective biomarkers of the aging process and/or cellular fitness. Accordingly in certain embodiments, methods are provided for detecting and/or quantifying replicative and/or genotoxic stress-induced senescence of mammalian cells. The method typically involves detecting and/or quantifying methylation of histone H1 at residue 172 and/or at histone H1 residue 180 in a biological sample comprising said cell or tissue, wherein methylation of histone H1 at residue 172 and/or at histone H1 residue 180 is a marker replicative and/or genotoxic stress-induced senescence of the cell(s) and/or cellular fitness. Suitable biological samples include, but are not limited to primary cell or tissue samples, histological samples, biopsy samples, and the like.

Data is also provided indicating that treatment with rapamycin blocks H1.0 eviction from chromatin and accumulation of its the meK172meK180 methylated form in cytoplasm, indicating that a meK172 and/or meK180 H1.0 survey of different cellular models can be informative for screening anti-aging compounds. Accordingly in certain embodiments, a method is provided for identifying compounds that have anti-aging activity. The method typically involves contacting test cells (e.g., in vitro, in vivo) with one or more test agents; and detecting and/or quantifying methylation of histone H1 at residue 172 and/or at histone H1 residue 180 in the cells (or in a tissue comprising the cells); and scoring test agents that reduce methylation of histone H1 at residue 172 and/or at histone H1 residue 180 in the cells as compared to (negative) control cells as candidate compounds that have anti-aging activity and/or increase cellular fitness. In various embodiments the contacting can comprise administering test compounds to a test animal, contacting cells in primary cultures, contacting cells in highly passaged cultures, contacting cells in established cell lines, contacting cells in histological samples, contacting cells from biopsy samples, and the like.

Cellular senescence is believed to be associated with accumulation of persistent DNA damage and activation of DNA damage response (DDR) pathways. In the DDR pathway, some chromatin modifications seem to play a critical role in marking lesions or recruiting factors involved in repair, thus facilitating the function of repair proteins. The best characterized in this context are histone H2AX and H1 phosphorylation events. We were successful in demonstrating previously unreported dynamics of histone H1.0 associated with replicative and genotoxic stress-induced senescence of human adult stem cells. By using immunostaining and western blot analysis we were able to demonstrate significant loss of the histone H1.0 from chromatin upon adult stem cells aging. This loss is accompanied by accumulation of meK172meK180 methylated form of H1.0 in the cytoplasm. Additionally, we have demonstrated that such methylation of histone H1 is associated with initial DNA damage response (DDR), since treatment with bleomycin (50 µg/ml) triggers nuclear meK172meK180 H1 methylation, and these PTMs co-localize with γH2AX, associated with DNA double-stranded breaks. Surprisingly, the recovery after DNA damage in our time course experiments points to two independent events: 1) a complete recovery from the DNA damage: clearing the DNA damage sites (loss of γH2AX) and meK172meK180 H1 markers; and 2) a cellular senescence accompanied by time-dependent persistent γH2AX-focus forming activity, time-dependent eviction of meK172meK180 H1 from chromatin and accumulation of meK172meK180 H1 in cytoplasm. Our experiments demonstrate that treatment of the either human somatic HCA2 cells or stem hADSC cells with rapamycin 24 hrs prior to bleomicin-induced DNA damage blocks meK172meK180 methylated form of H1.0 in the cytoplasm, and therefore H1.0 PTMs can be used as biomarker(s) of cell fitness and/or biomarker of success upon chemotherapy in cancer treatments.

In particular, it is noted that many chemotherapeutics act by forcing rapidly dividing cancer cells into cellular senescence. The appropriate type of drug or combination of drugs as well as proper dosage determination varies from patient to patient. Methods to compare outcomes of drug selection efficiency, patient specific induction regimens and drug performance status remain problematic. Currently, there are no diagnostic tools available to monitor (unbiased and quantitatively) the efficiency of senescence induction at a given dosage, therefore the relative benefit of the intense initial drug combination and dosage selection strategies remains uncertain.

The discovery of novel post translational modifications (K172 and/or K180 methylation) on histone H1 described herein and the antibodies described herein that are selective for these PTMs, allow for the quick and efficient detection of the proportion of cells that exit the proliferative state and enter cellular senescence. Therefore, the compositions and methods described herein provide efficient tools for the monitoring of chemotherapy regimens in a clinical setting.

Accordingly, in certain embodiments, a method of monitoring a chemotherapeutic regimen in a subject is provided. The method typically involves detecting and/or quantifying methylation of cancer cells in a sample derived from the subject and increasing the chemotherapeutic dosage regimen to a level where cancer cells comprising the sample show methylation of histone H1 at residue 172 and/or at residue 180 and/or to a level where cancer cells comprising the sample show methylation of an H1 histone isoform at residues corresponding to H1 residues 172 and/or 189. In certain embodiments, the dosage regimen is altered so that at least 10%, or at least 20%, or at least 30%, or at least 40%, or at least 50%, or at least 60%, or at least 70%, or at least 80%, or at least 90% of all the cells in the sample show methylation of histone H1 at residue 172 and/or at histone H1 residue 180. In certain embodiments, the dosage regimen is altered so that at least 10%, or at least 20%, or at least 30%, or at least 40%, or at least 50%, or at least 60%, or at least 70%, or at least 80%, or at least 90% of all the cancer cells in the sample show methylation of histone H1 at residue 172 and/or at histone H1 residue 180.

In another aspect a method of monitoring a chemotherapeutic regimen in a subject is provided that involves detecting and/or quantifying methylation of histone H1 at residue 172 and/or at histone H1 residue 180 in a biological sample derived from the subject detect; and decreasing the chemotherapeutic dosage regimen where normal (non-cancer cells) comprising the sample show decreased or no methylation of histone H1 at residue 172 and/or at residue 180 and/or decreased or no methylation of a histone H1 isoform at residues corresponding to H1 residues 172 and/or 180. In certain embodiments, the dosage regimen is altered so that at least 10%, or at least 20%, or at least 30%, or at least 40%, or at least 50%, or at least 60%, or at least 70%, or at least 80%, or at least 90% of the normal cells in the sample show no methylation of histone H1 at residue 172 and/or at histone H1 residue 180 and/or show no methylation of a histone H1 isoform a residues corresponding to H1 residues 172 and/or 180.

In certain embodiments a method of monitoring the efficiency of senescence induction in cancer cells in a subject at a given chemotherapeutic dosage regimen is provided. The method typically involves detecting and/or quantifying methylation of histone H1 at residue 172 and/or at histone H1 residue 180 and/or detecting and/or quantifying methylation of a histone H1 isoform at residues corresponding to H1 residues 172 and/or 180, in a biological sample comprising cancer cells derived from said subject where the ratio of cells showing methylation of histone H1 at residue 172 and/or at histone H1 residue 180 and/or an H1 isoform showing methylation at residues corresponding to H1 residues 172 and/or 180 compared to cells not showing such methylation provides a measure of the efficiency of senescence induction at that dosage regimen.

In addition, a set of versatile reagents were developed to test the biological relevance of meK172 and/or meK180 H1.0. In particular, anti-methyl-KH1.0 antibodies were developed. Ten to thirteen amino acid synthetic peptides corresponding to the region of 170-182 aa of H1.0 were used. The synthesis of the peptides was performed on an Applied Biosystems 443peptide synthesizer by standard Fmoc-Strategy at Thermo Fisher. We used single (AKPVKASKP-KKAKPVKmePKC, SEQ ID NO:1); AKPVKASKmeP-KKAKPVKPKC, (SEQ ID NO:2), and double modification (AKPVKASKmePKKAKPVKmePKC, (SEQ ID NO: 3) peptides linked to the immunogenic carrier KLH for mouse and guinea pig immunization using standard protocols. The quality and titer of generated antibodies were assessed by Dot Blot hybridization with synthetic peptides and Western Blot against endogenous H1.0 in the extracts from human ADSCs. It was demonstrated that that both anti-meK172H1.0 and meK172meK180 H1.0 antibodies recognize a single epitope of expected for H1.0 size (20 kDa). Accordingly, in various embodiments, antibodies that specifically or preferentially bind to a H1 histone methylated at residue 172 and/or residue 180 are provided. The antibodies are readily used in a variety of immunoassays including, but not limited to of ELISA, Western blot, flow cytometry, a lateral flow immunoassay, a magnetic immunoassay, a radioimmunoassay, surround Optical Fiber Immunoassay (SOFIA), and the like.

Detection of Methylation of Histone H1.

In various embodiments methods of detecting senescence, and or DNA damage of a cell in a biological sample are provided. The methods entail that entails detecting the methylation of histone H1 (H1.0) at residue 172 and/or at residue 180 (wherein H1 residues are numbered according to human H1) and/or methylation of an H1 isoform at residues corresponding to H1 residues 172 and/or 180. Methylation at either, or both, of these sites is a biomarker of cell fitness and/or a biomarker of success upon chemotherapy in cancer treatment, and/or a marker of DNA damage (e.g., in coincidence with γH2AX deposition), and/or an indicator of replicative and genotoxic stress-induced senescence (e.g., a biomarker of the aging process and/or of cellular fitness).

In various embodiments detection of methylation of histone H1 at residue 172 and/or residue 180 can be qualitative or quantitative, but is preferably quantitative. In certain embodiments illustrative embodiments, the amount of methylated H1 (at residue 172 and/or residue 180) can be compared with the amount in a control sample. In certain illustrative embodiments the test and control samples can be any two samples that one wishes to compare.

H1 methylation at residue 172 and/or residue 180 (or methylation of an H1 isoform at residues corresponding to H1 residues 172 and/or 180) can be detected in vivo or in vitro. However, methylation assays are generally more conveniently carried out in vitro, for example, in a biological sample (e.g., whole blood, plasma, serum, saliva, synovial fluid, cerebrospinal fluid, bronchial lavage, ascites fluid, bone marrow aspirate, pleural effusion, urine, or tissue, cells, or fractions thereof) derived from a subject (e.g., a human or a non-human mammal). In certain embodiments, suitable biological samples include, but are not limited to primary cell or tissue samples, histological samples, biopsy samples, and the like.

Although the sample is typically taken from a human, the assays can be used to detect H1 methylation at residue 172 and/or 180 (or H1 isoform methylation at residues corresponding to H1 residues 172 and/or 180) in cells from any organism that produces this protein. Thus, the methods described herein can be performed on samples from eukaryotes; particularly vertebrates; more particularly mammals, such as dogs, cats, sheep, cattle and pigs; and most particularly primates, such as humans, chimpanzees, gorillas, macaques, and baboons, and rodents such as mice, rats, and guinea pigs, and/or in cell culture, histological samples, biopsies, and the like.

Tissue or fluid samples are obtained according to standard methods well known to those of skill in the art, such as, for example, by biopsy or venipuncture. The sample is optionally pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

Methylation of histone H1 (H1.0) at residue 172 and/or 180 can be detected and quantified by any of a number of other means well known to those of skill in the art. These can entail analytic biochemical methods such as spectrophotometry, radiography, electrophoresis, capillary electrophoresis, high performance liquid chromatography (HPLC), thin layer chromatography (TLC), hyperdiffusion chromatography, and the like, in addition to various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, mass spectrometry, and the like.

Immunoassays

In certain preferred embodiments, methylation of histone H1 (H1.0) at residue 172 and/or 180 is detected using an immunoassay in which a biological sample comprising H1 (H1.0) is contacted with an antibody specific for H1 or a fragment thereof methylated at residue 172 and/or 180 under conditions suitable for antibody binding, followed by detection of antibody binding. Such assays require an antibody that preferentially binds these methylated forms of H1 over the non-methylated forms or other proteins. Suitable antibodies are described in greater detail below.

Using the antibodies described herein, H1 (H1.0) methylated as described herein can be detected and optionally quantified using any of a number of well recognized immunological binding assays (see, e.g., U.S. Pat. Nos. 4,366,241; 4,376, 110; 4,517,288; and 4,837,168, and the like). Such assays include, but are not limited to ELISA, Western blot, flow cytometry, a lateral flow immunoassay, a magnetic immunoassay, a radioimmunoassay, surround Optical Fiber Immunoassay (SOFIA), and the like. For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991)).

The immunoassays described herein can be performed in any of a number configurations, e.g., those reviewed in Maggio (ed.) (1980) Enzyme Immunoassay CRC Press, Boca Raton, Fla.; Tijan (1985) "Practice and Theory of Enzyme Immunoassays," Laboratory Techniques in Biochemistry and Molecular Biology, Elsevier Science Publishers B.V., Amsterdam; Harlow and Lane, supra; Chan (ed.) (1987) Immunoassay: A Practical Guide Academic Press, Orlando, Fla.; Price and Newman (eds.) (1991) Principles and Practice of Immunoassays Stockton Press, NY; and Ngo (ed.) (1988) Non isotopic Immunoassays Plenum Press, NY.

Immunoassays often utilize a labeling agent to specifically bind to and label the binding complex formed by the antibody and the analyte (e.g., an antibody/H1 meK172meK180 complex). In certain embodiments the labeling agent may itself be one of the moieties comprising the antibody/analyte complex. Thus, the labeling agent may be a labeled anti-H1-meK172meK180 antibody. Alternatively, the labeling agent can be a third moiety, such as another antibody, that specifically binds to the anti-methylated H1 antibody, the antibody/H1q complex, or to a group (e.g., biotin) that is covalently linked to the anti-methylated H1 antibody.

In one embodiment, the labeling agent is an antibody that specifically binds to the anti-methylated H1 antibody. Such agents are well known to those of skill in the art, and most typically comprise labeled antibodies that specifically bind antibodies of the particular animal species from which the anti-methylated H1 antibody is derived (e.g., an anti-species antibody). Thus, for example, where the anti-methylated H1 antibody is a rabbit antibody, the labeling agent may be a mouse anti-rabbit IgG (i.e., an antibody specific to the constant region of the rabbit antibody).

Other proteins capable of specifically binding immunoglobulin constant regions, such as streptococcal protein A or protein G can also used as the labeling agent. These proteins are normal constituents of the cell walls of streptococcal bacteria. They exhibit a strong non-immunogenic reactivity with immunoglobulin constant regions from a variety of species (see generally Kronval et al. (1973) *J. Immunol.*, 111: 1401-1406, and Akerstrom et al. (1985) *J. Immunol.*, 135: 2589-2542, and the like).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, volume of solution, concentrations, and the like. Usually, the assays are carried out at ambient temperature, although they can be conducted over a range of temperatures, such as 5° C. 45° C.

Non Competitive Assay Formats

Immunoassays for detecting are preferably either competitive or noncompetitive. Noncompetitive immunoassays are assays in which the amount of captured analyte (in this case, methylated H1 (or fragments thereof) is directly measured. In one preferred "sandwich" assay, for example, the capture agent (e.g., one or more of the antibodies described herein) are bound directly or indirectly to a solid substrate, where they are immobilized. These immobilized anti-methylated H1 antibodies capture H1 meK172meK180 or fragments thereof comprising meK172 and/or meK180 present in a sample. The histone or histone fragment thus immobilized is then bound by a labeling agent, such as an anti-H1 antibody bearing a label. Alternatively, the second antibody may lack a label, but it may, in turn, be bound by a labeled third antibody specific for antibodies of the species from which the second antibody is derived. Free, labeled antibody is washed away, and the remaining bound labeled antibody is detected.

Competitive Assay Formats

In competitive assays, the amount of analyte (e.g., H1 meK172 and/or meK180) present in the sample is measured indirectly by measuring the amount of an added (exogenous) analyte displaced (or competed away) from a capture agent (e.g., an antibody directed to the meK172 and/or meK180 domain) by the analyte present in the sample. In one competitive assay, a known amount of methylated H1 is added to a test sample with an unquantified amount of methylated H1, and the sample is contacted with the capture agent (e.g., the antibodies described herein). The amount of added methylated H1 that binds to the anti methylated H1 antibody is inversely proportional to the concentration of methylated H1 present in the test sample.

As noted above, the antibodies described herein (e.g. anti-H1 meK172 and/or meK180) can be immobilized on a solid substrate to facilitate bound versus free separation. The amount of methylated H1 meK172 and/or meK180 bound to the immobilized antibody is determined either by measuring the amount of H1 present in the immune complex, or alternatively by measuring the amount of free (uncomplexed) methylated H1.

Western Blots

Western blot analysis and related methods can conveniently be used to detect and quantify the presence of H1 methylated at residue 172 and/or residue 180 (or relevant fragments thereof) in a sample. The technique generally comprises separating sample products by gel electrophoresis on the basis of molecular weight, transferring the separated products to a suitable solid support, (such as a nitrocellulose filter, a nylon filter, or derivatized nylon filter), and incubating the sample with the antibodies that specifically bind H1 meK172 and/or meK180. These antibodies can be directly labeled or alternatively can be subsequently detected using labeled secondary antibodies that specifically bind to the anti-H1 meK172 and/or meK180 antibody.

Substrates

As mentioned above, depending upon the assay, a component, such as an anti-H1 meK172 and/or meK180 antibody, can be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non-specific binding, simplify covalent conjugation, enhance signal detection or the like.

If covalent bonding between a component and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature (see, e.g., Immobilized Enzymes, Ichiro Chibata, Halsted Press, New York, 1978; and Cuatrecasas, (1970) *J. Biol. Chem.* 245 3059; and the like).

In addition to covalent bonding, various methods for noncovalently binding an assay component can be used. Noncovalent binding is typically nonspecific absorption of a component to the surface. Typically, the surface is blocked with a second component to prevent nonspecific binding of labeled assay components. Alternatively, the surface is designed such that it nonspecifically binds one component but does not significantly bind another. For example, a surface bearing a lectin such as concanavalin A will bind a carbohydrate-containing compound but not a labeled protein that lacks glycosylation. Various solid surfaces for use in noncovalent attachment of assay components are reviewed in U.S. Pat. Nos. 4,447,576 and 4,254,082.

Reduction of Non Specific Binding

One of skill will appreciate that it is often desirable to reduce non specific binding in immunoassays and during analyte purification. Where the assay involves anti-H1 meK172 and/or meK180 antibodies, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

Detection

Detection of methylation is carried out by any known method. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. DYNABEADS®), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., LacZ, CAT, horseradish peroxidase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads.

The label can be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

Components can also be conjugated directly to signal-generating compounds, e.g., by conjugation with an enzyme or fluorophore. Enzymes of interest as labels will primarily be hydrolases, particularly phosphatases, esterases and glycosidases, or oxitranscription factoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Antibodies Specific for Histone H1 Methylated at Residue 172, at Residue 180, or at Both Residues.

In certain embodiments, antibodies are provided that are specific for histone H1 (H1.0) comprising a methyl on residue K172, on residue K180, or on both residues, wherein H1 residues are numbered according to human H1. The invention encompasses antibodies that are specific for these methylated H1 proteins or fragments any species, e.g., any eukaryote, and particularly vertebrate. However, antibodies specific for H1 meK172 and/or meK180 from mammals are preferred and those specific for human H1 meK172 and/or meK180 or fragments thereof are more preferred.

In certain embodiments the antibodies can be specific for H1 meK172 and/or meK180 from one species or can cross-react with H1 meK172 and/or meK180 from multiple species. Antibodies of the invention preferentially bind H1 histone or histone fragment comprising a methyl on residue 172, on residue 180, or on both residues over the form lacking a methyl group(s) at these residues or other proteins. The degree of preferential binding should be sufficient to allow use of the antibody to distinguish H1 meK172 and/or meK180 or fragments thereof from the form that is not methylated at these residues under normal assay conditions, such as those described herein. In various embodiments the binding preference (e.g., affinity) for the H1 meK172 and/or meK180 is generally at least about 2-fold, more preferably at least about 5-fold, and most preferably at least about 10-, 20-, 50-, $10^2$-, $10^3$-, $10^4$, $10^5$, or $10^6$-fold over a non-specific target molecule (e.g. a randomly generated molecule lacking the specifically recognized site(s)). Antibodies of the invention preferably have a binding affinity of about $10^{-6}$, about $10^{-7}$, about $10^{-8}$ or better.

In various embodiments the invention encompasses polyclonal and monoclonal anti-H1 meK172 and/or meK180 antibodies. Polyclonal antibodies are raised by injecting (e.g. subcutaneous or intramuscular injection) antigenic polypeptides into a suitable mammal (e.g., a mouse or a rabbit). Generally, the polypeptide used to raise anti-H1 meK172 and/or meK180 should induce production of high titers of antibody with relatively high affinity for H1 meK172 and/or meK180.

If desired, the immunizing polypeptide may be conjugated to a carrier protein by conjugation using techniques that are well known in the art. Commonly used carriers include keyhole limpet hemocyanin (KLH), thyroglobulin, bovine serum albumin (BSA), and tetanus toxoid. The conjugate is then used to immunize the animal.

In one illustrative, but non-limiting embodiment, single (AKPVKASKPKKAKPVKmePKC (SEQ ID NO:1; AKPVKASKmePKKAKPVKPKC (SEQ ID NO: 2) and double modification (AKPVKASKmePKKAKPVKmePKC (SEQ ID NO: 3) peptides linked to the immunogenic carrier KLH 58 were used for mouse and guinea pig immunization using standard protocols. The quality and titre of generated antibodies were assessed by Dot Blot hybridization with synthetic peptides and Western Blot against endogenous H1.0 in the extracts from human ADSCs. Both anti-meK172H1.0 and meK172meK180 H1.0 antibodies recognize a single epitope of expected for H1.0 size (20 kDa).

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience).

In certain embodiments, polyclonal anti-H1 meK172 and/or meK180 antibodies are subjected to two affinity purification steps. First, the polyclonal antiserum is contacted with an anti-H1 meK172 and/or meK180 polypeptide, and the fraction that binds is recovered. This fraction is then contacted with an H1 polypeptide that is not methylated at residue 172 and/or 180, and the fraction that fails to bind to the unmethylated form is recovered to obtain a polyclonal antiserum that is specific for anti-H1 meK172 and/or meK180 (see, Examples).

For many applications, monoclonal anti-H1 meK172 and/or meK180 antibodies are preferred. The general method used for production of hybridomas secreting mAbs is well known (Kohler and Milstein (1975) *Nature,* 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAb's can be accomplished using relatively routine screening techniques (such as the enzyme-linked immunosorbent assay, or "ELISA") to determine the elementary reaction pattern of the mAb of interest.

It is also possible to evaluate a mAb to determine whether it has the same specificity as a mAb described herein without undue experimentation by determining whether the mAb being tested prevents the described mAb from binding a target polypeptide. If the mAb being tested competes with the mAb described herein, it is likely that the two monoclonal antibodies bind to the same or a closely related epitope. Still another way to determine whether a mAb has the specificity of a mAb described herein is to preincubate the mAb described herein with an antigen with which it is normally reactive, and determine if the mAb being tested is inhibited in its ability to bind the antigen. Such inhibition indicates that the mAb being tested has the same, or a closely related, epitopic specificity as the mAb described herein.

The anti-methylated H1.0 antibodies of contemplated herein include single chain Fv ("scFv") polypeptides, which may be expressed from a nucleic acid including $V_H$- and $V_L$-encoding sequences either joined directly or joined by a peptide-encoding linker (see, e.g., Huston, et al. (1988) *Proc. Nat. Acad. Sci. USA,* 85: 5879-5883). There are a number of structures for converting the naturally aggregated, but chemically separated, light and heavy polypeptide chains from an antibody V region into an scFv molecule which will fold into a three dimensional structure substantially similar to the structure of an antigen-binding site (see, e.g, U.S. Pat. Nos. 5,091,513, 5,132,405, 4,956,778, and the like).

Design criteria include determination of the appropriate length to span the distance between the C-terminus of one chain and the N-terminus of the other, wherein the linker is generally formed from small hydrophilic amino acid residues that do not tend to coil or form secondary structures. Such methods have been described in the art (see e.g., U.S. Pat. Nos. 5,091,513 and 5,132,405 to Huston et al.; and U.S. Pat. No. 4,946,778 to Ladner et al.).

In this regard, the first general step of linker design involves identification of plausible sites to be linked. Appropriate linkage sites on each of the $V_H$ and $V_L$ polypeptide domains include those that will result in the minimum loss of residues from the polypeptide domains, and that will necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and preferably are free of residues having large side groups which might interfere with proper folding of the $V_H$ and $V_L$ chains. Thus, suitable linkers under the invention generally comprise polypeptide chains of alternating sets of glycine and serine residues and may include glutamic acid and lysine residues inserted to enhance solubility. One illustrative and useful the invention has the amino acid sequence $((Gly)_4Ser)_3$ (SEQ ID NO:6). Another illustrative linker has the amino acid sequence comprising 2 or 3 repeats of $((Ser)_4Gly)$ (SEQ ID NO:7) such as $((Ser)_4Gly)_3$ (SEQ ID NO:8). Nucleotide sequences encoding such linker moieties can be readily provided using various oligonucleotide synthesis techniques known in the art.

Single chain antibodies (scFv or others), can be produced/selected using phage display or yeast display technology. The ability to express antibody fragments on the surface of viruses that infect bacteria (bacteriophage or phage) makes it possible to isolate a single binding antibody fragment, e.g., from a library of greater than 10.sup.10 nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) *Nucleic Acids Res.* 19: 4133-4137).

Since the antibody fragments on the surface of the phage are functional, phage bearing antigen binding antibody fragments can be separated from non-binding phage by antigen affinity chromatography (McCafferty et al. (1990) *Nature,* 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) *Nature,* 348: 552-554). Thus, even when enrichments are low (Marks et al. (1991) *J. Mol. Biol.* 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Monovalent scFv antibodies can be converted to bivalent $(scFv')_2$ antibodies, in which two scFv chains are linked covalently or noncovalently. For example, de Kruif and Logtenberg (1996) *J. Biol. Chem.* 271:7630-7634 describes the construction of leucine zipper-based dimerization cassettes for the conversion of recombinant scFv antibodies to $(scFv')_2$ antibodies. A truncated murine IgG3 hinge region and a Fos or Jun leucine zipper were cloned into four scFv fragments. Cysteine residues flanking the zipper region were introduced to covalently link dimerized scFv fragments. The secreted fusion proteins were shown to form stable Fos-Fos or Jun-Jun homodimers.

Human antibodies can be produced without prior immunization by displaying very large and diverse V-gene repertoires on phage (Marks et al. (1991) *J. Mol. Biol.* 222: 581-597). In one embodiment natural VH and VL repertoires present in human peripheral blood lymphocytes are isolated from unimmunized donors by PCR. The V-gene repertoires were spliced together at random using PCR to create a scFv gene repertoire which was cloned into a phage vector to create a library of 30 million phage antibodies. From this single "naive" phage antibody library, binding antibody fragments have been isolated against more than 17 different antigens, including haptens, polysaccharides and proteins (Marks et al. (1991) *J. Mol. Biol.* 222: 581-597; Marks et al. (1993). *Bio/Technology*, 10: 779-783; Griffiths et al. (1993) *EMBO J.* 12: 725-734; Clackson et al. (1991) *Nature* 352: 624-628). Antibodies have been produced against self proteins, including human thyroglobulin, immunoglobulin, tumor necrosis factor and CEA (Griffiths et al. (1993) *EMBO J.* 12: 725-734). It is also possible to isolate antibodies against cell surface antigens by selecting directly on intact cells. The antibody fragments are highly specific for the antigen used for selection and have affinities in the 1 nM to 100 nM range (Marks et al. (1991) *J. Mol. Biol.* 222: 581-597; Griffiths et al. (1993) *EMBO J.* 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley antibody laboratories, Bethyl Laboratories, Anawa, Eurogenetec, etc.).

Kits

In another embodiment, the invention provides a kit useful for the detection of methylation of H1 (H1.0) at residue 172 and/or residue 180. Kits will typically comprise one or more anti-H1 meK172 and/or meK180 antibodies as described herein. In certain embodiments the antibody(s) can be labeled. In addition, the kits can optionally include instructional materials for carrying out any of the methods described herein. While the instructional materials typically comprise written or printed materials, they are not limited to such. Any medium capable of storing such instructions and communicating them to an end user is contemplated herein. Such media include, but are not limited to, electronic storage media (e.g., magnetic discs, tapes, cartridges, chips), optical media (e.g., CD ROM), and the like. Such media can include addresses to internet sites that provide such instructional materials.

The kits may also include additional components to facilitate the particular application for which the kit is designed. Thus, for example, where a kit contains an anti-anti-H1 meK172 and/or meK180 that is labeled, the kit may additionally contain means of detecting the label (e.g., enzyme substrates for enzymatic labels, filter sets to detect fluorescent labels, appropriate secondary labels, or the like). The kits may additionally include buffers and other reagents routinely used for the practice of a particular method. An exemplary kit useful in an immunoassay to detect methylation of H1 (H1.0) at residue 172 and/or residue 180 include, in addition to an anti-H1 meK172 and/or meK180 antibody, an H1 peptide or polypeptide that includes a methyl at residue 172 and/or 180. This peptide or polypeptide can be employed, for example, as a positive control or as competitor in a competitive immunoassay, and can be labeled or not, depending on the format of the assay to be carried out.

EXAMPLES

The following examples are offered to illustrate, but not to limit the claimed invention.

Example 1

Discovery of New Aging-Related Histone Post-Translational Modifications

Since a majority of signaling pathways converge in chromatin$_{17,58}$ resulting in the regulation of gene transcription outcome, it is reasonable to suggest that the decline of cellular and tissue fitness with aging is somewhat recorded in histone PTMs. With this in mind, a deep proteomic analysis was performed to identify novel PTMs in histones associated with replicative senescence of human adult adipose derived stem cells (hADSC). Previously unreported combinatorial modifications in histones were identified.

ADSCs as a Model System.

The primary model system used in this example is adipose derived stem cells (ADSCs). These cells can be easily obtained, easily purified, and are readily expanded in culture (Wang et al. (2011) *Cell Cycle* 10: 3016-3030). ADSCs have been shown to be very similar in morphology and phenotype to marrow-derived stem cells, and upon receipt of the appropriate chemical stimulus, they have been demonstrated to differentiate into cells of multiple lineages (Strem et al. (2005) *Keio J Med.*, 54: 132-141; Cai et al. (2009) *Stem Cells*, 27: 230-237; Bacou et al. (2004) *Cell Transplant* 13: 103-111; Mizuno (2002) *Curr. Opin. Mol. Ther.*, 12: 442-449; Zuk et al. (2001) *Tissue Eng.*, 7: 211-228). A number of major publications indicated that ADSCs are an effective system to study many biological processes, such as DNA repair, cellular senescence, transcriptional regulation, and epigenetic properties of chromatin (Wang et al. (2011) *Cell Cycle* 10: 3016-3030 (2011); Tollervey and Lunyak (2011) *Cell Cycle* 10: 4173-4176; Tran and Kahn (2010) *Nat Rev Endocrinol.*, 6: 195-213; Scaffidi et al. (208) *Nat. Cell. Biol.*, 10: 452-459; Sepe et al. (2001) *J. Cell Physiol.*, 189: 54-63). By contrast to most other human adult stem cells (e.g. neural cortical progenitors NCP, bone-marrow-derived hematopoietic stem cells HSC), those from adipose tissue can be readily isolated from generally healthy donors without undue risks, thus making an expandable sample collection possible at relatively low expense.

Fat tissue harvesting occurs through voluntarily routine subcutaneous fat aspiration (liposuction), and the purity of isolated ADSCs is confirmable by flow cytometric analysis. Cells were collected that do not express endothelial or hematopoietic markers, e.g. purified ADSCs negative for CD31, CD106, CD184, CD34, and CD45 cell surface antigens, but positive for stromal cell markers CD 105 and CD4464, 68-70. The yield of adult stem cell recovery from primary lipoaspirate was about $10^5$ cells from 100 ml of fat tissue. ADSCs extracted from lypoaspirates have a very stable immunophenotype at various stages of isolation, purification and expansion (Mitchell et al. (2006) *Stem Cells*, 24: 376-385).

ADSCs are a useful model system for studying mechanisms of aging since they have not been classified as immortal. Adipose tissue is known to vary in metabolic activity and in its capacity for proliferation and differentiation, depending on the age and gender of the patient (Tran and Kahn (2010) *Nat Rev Endocrinol.*, 6: 195-213; Tholpady et al. (2006) *Clin Plast Surg* 33: 55-62). Additionally, ADSCs display obvious signs of "old age" when passaged ex vivo (Wang et al. (2011)

Cell Cycle 10: 3016-3030; Tran and Kahn (2010) *Nat Rev Endocrinol.*, 6: 195-213). The culture's morphological abnormalities are typical of the Hayflick model of cellular aging (Juckett (1987) *Mech Ageing Dev* 38: 49-71). Around 30 population doublings, cells gradually cease proliferation and express senescence associated β-galactosidase (Wang et al. (2011) *Cell Cycle* 10: 3016-3030). These cells are limited in capacity for sub-culturing due to what is thought to be replicative senescence associated with accumulation of DNA damage (Id.). It is believed that the accumulation of DNA damage may play an essential role in both cellular senescence and organismal aging (Wang et al. (2011) *Cell Cycle* 10: 3016-3030; Sedelnikova et al. (2008) *Aging Cell* 7: 89-100). Phosphorylation of serine 129 of histone H2AX (ãH2AX), which occurs specifically at sites of DNA double-strand breaks (DSBs) (Tanaka et al. (2006) *Cell Prolif.*, 39: 313-323) triggers persistent DNA damage (Rodier et al. (2009) *Nat. Cell Biol.*, 11: 973-979) and activates DNA damage response (DDR) pathways (Wang et al. (2011) *Cell Cycle* 10: 3016-3030; Sedelnikova et al. (2004) *Nat. Cell Biol.*, 6: 168-170; van Attikum and Gasser 9205) *Nat. Rev. Mol. Cell. Biol.*, 6: 757-765; Shiloh et al. (2003) *Nat. Rev. Cancer*, 3: 155-168; Herbig et al. (2004) *Molecular Cell*, 14: 501-513; d'Adda et al. (2003) *Nature* 426: 194-198).

Discovery of New Aging-Related Histone PTMs in Human ADSCs by Deep Mass Spectrometry.

In order to better understand changes in chromatin structure related to the onset of adult stem cells aging, post-translational modifications of histones was assessed by using M/Z Pair Tag LC-MS. The deep proteomic analysis revealed new, previously not reported, combinatorial sets of PTMs (acetylation, methylation, propionylation and phosphorylation), which occur in histones only upon the onset of ADSC senescence. Five technical replicate injections of self-renewing and senescent ADSC lysates were processed in a full-scan optimized configuration. It was determined that the chromatography and instrument methods for optimal full scan quantitative measurements conflicted with methods of optimal fragmentation scans. Therefore the mass spectrometer's accurate mass and broad dynamic range capabilities were exploited by incorporating into analysis two distinct passes of data measurement. The first pass focused upon acquiring un-compromised and optimized full scan (MS) data for highly reproducible quantification. This first full-scan quantitative pass was used to generate an inclusion list of potentially interesting features. The inclusion list was then used for targeted fragmentation scan acquisition during a second pass for a subset of the data samples. This approach was extremely fruitful and resulted in the identification of new combinatorial patterns of the modifications occurring on histones H1.0 meK172meK180 H1.0 (see, e.g., FIG. 1) have not been previously reported in conjunction with possible outcomes of either somatic or stem cells aging (replicative or genotoxic stress-induced senescence) as well as under conditions of acute DNA damage.

Antibodies

Figure 2A:
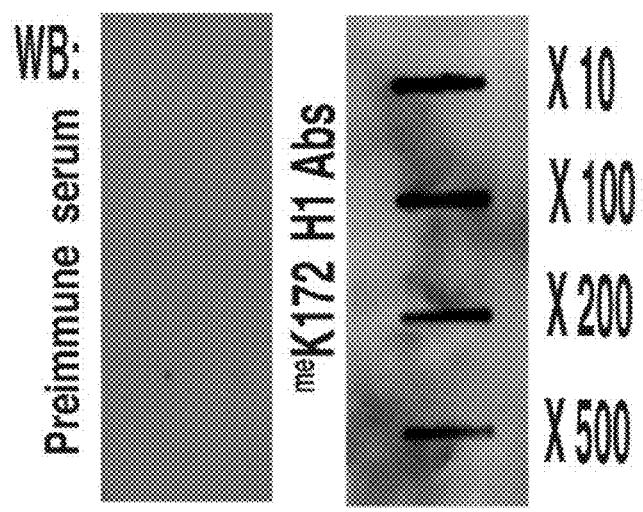
FIGS. 2A-2C illustrate validation of antibody specificity against histone H1 methylated form.
Figure 2B:
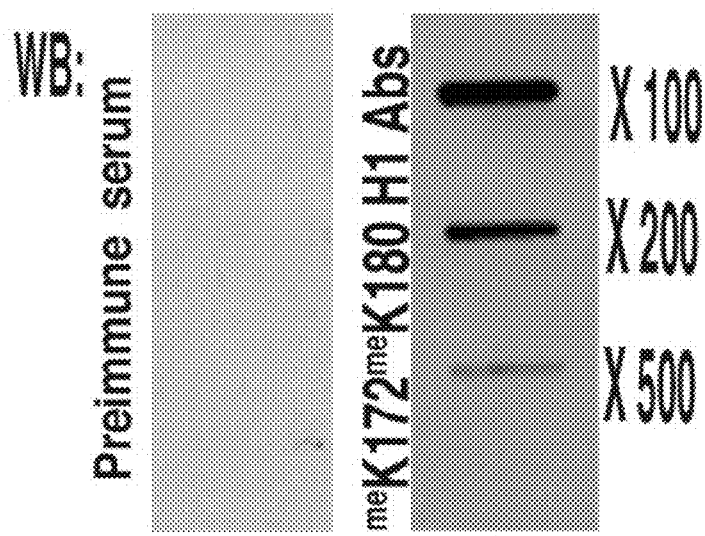
Figure 2C:
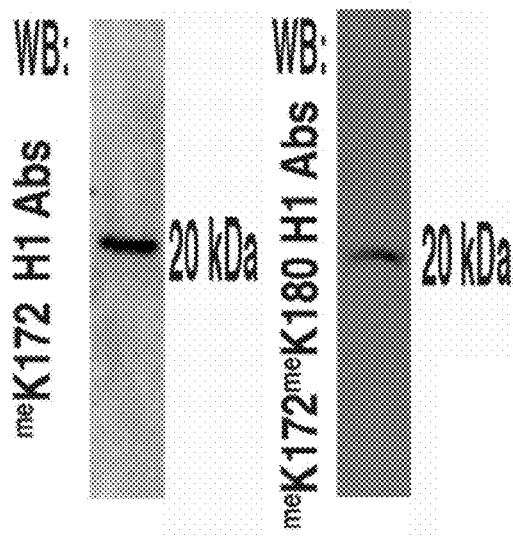

To test the biological relevance of meK172meK180 H1.0, anti-methyl-KH1.0 antibodies were generated. To produce the antibodies, 10-13 mer synthetic peptides corresponding to the region of 170-182 aa of H1.0 were used as antigens. The synthesis of the peptides was performed on an Applied Biosystems 443 peptide synthesizer by standard Fmoc-Strategy at Thermo Fisher. Single (AKPVKASKPKKAKPVKme-PKC (SEQ ID NO:1); AKPVKASKmePKKAKPVKPKC (SEQ ID NO:2)), and double modification (AKPVKASKme-PKKAKPVKmePKC (SEQ ID NO:3)) peptides linked to the immunogenic carrier KLH (Pagans et al. (2011) Methods 53: 91-96) were used for mouse and guinea pig immunization using standard protocols (Id.). The quality and titre of generated antibodies were assessed by Dot Blot hybridization with synthetic peptides and Western Blot against endogenous H1.0 in the extracts from human ADSCs. Results of these experiments are shown in FIGS. 2A-2C. We were able to demonstrate that both anti-meK172H1.0 and $^{me}$K172$^{me}$K180 H1.0 antibodies recognize a single epitope of expected for H1.0 protein (20 kDa). It is believed these are the first antibodies specific for the post-translational modifications identified above. It is also believed these antibodies provide a set of versatile reagents for biochemical, cytological, genome-wide, and functional assessment of these H1.0 PTMs in humans, human adult stem cells biology, aging and disease.

Both Replicative and Genotoxic Stress-Induced Senescence of hADSCs are Associated with Loss of Histone H1.0 from Chromatin and Accumulation of the meK172-meK180 H1.0 Form in the Cytoplasm.

Figure 3A:
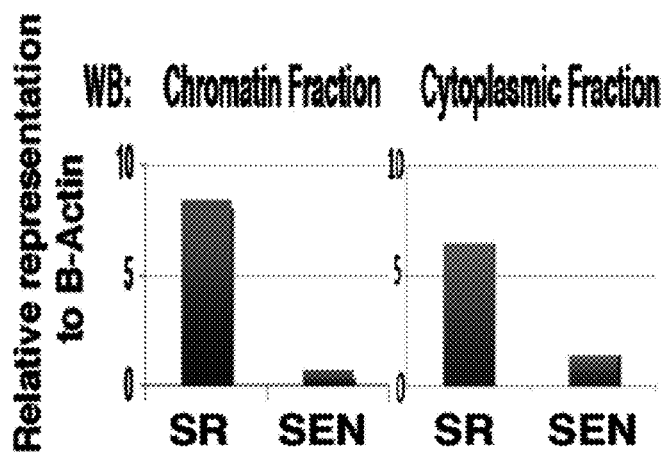
FIGS. 3A and 3B show Western blot and immunohistochemistry analysis of H1.0 eviction from the chromatin upon replicative senescence of human hADSCs accompanied by accumulation of $^{me}$K172$^{me}$K180 methylated form of H1.0 in the cytoplasm. SR-population doubling PD 11 and 15 represent selfrenewing stage of hADSCs, SEN-PD35 and 38 of hADSCs are characterized by cellular senescence as previously published (Wang et al. (2011) Cell Cycle 10: 3016-3030).
Figure 3B:
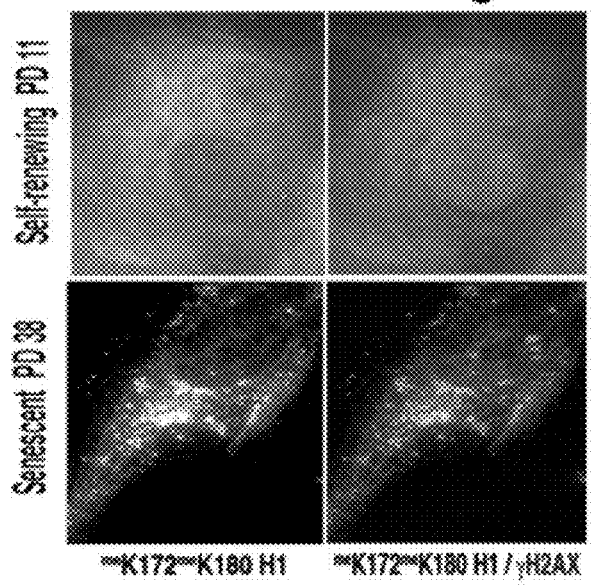
Figure 3C:
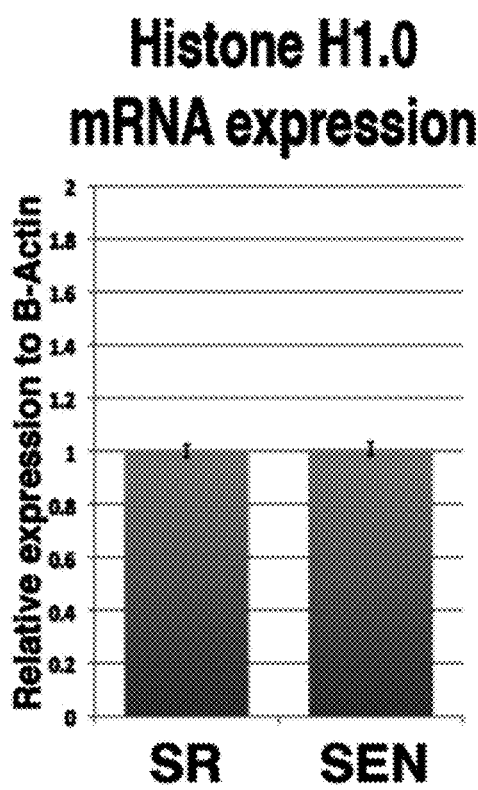
FIG. 3C: No changes in the expression of H1.0 gene were observed upon replication senescence.

Cellular senescence is believed to be associated with accumulation of persistent DNA damage (Sedelnikova et al. (2008) *Aging Cell* 7: 89-100; Rodier et al. (2009) *Nat. Cell Biol.*, 11: 973-979) and activation of DNA damage response (DDR) pathways (Wang et al. (2011) *Cell Cycle* 10: 3016-3030; Sedelnikova et al. (2004) *Nat. Cell Biol.*, 6: 168-170; Herbig et al. (2004) *Molecular Cell*, 14: 501-513; d'Adda et al. (2003) *Nature* 426: 194-198). In the DDR pathway, some chromatin modifications seem to play a critical role in marking lesions or recruiting factors involved in repair, thus facilitating the function of the repair proteins. The best characterized in this context are histone H2AX and H1 phosphorylation events (Ju et al. (2006) *Science*, 312: 1798-1802; van Attikum and Gasser (2005) *Nat. Rev. Mol. Cell. Biol.*, 6: 757-765). In a preliminary study, we were successful in demonstrating previously not reported dynamics of histone H1.0 associated with replicative and genotoxic stress-induced senescence of human adult stem and somatic cells. By using Western blot analysis (FIG. 3C) and immunostaining (FIG. 3B), a significant loss of the histone H1.0 from chromatin upon adult stem cells aging was demonstrated. This loss is accompanied by accumulation of meK172meK180 methylated form of H1.0 in the cytoplasm (FIG. 3B). No changes in H1.0 gene transcription activity were observed under condition of replicative senescence of hADSCs as indicated by qPCR experiments (FIG. 3C).

However, acute DNA damage results in results in drastic increase of H1.0 transcription (FIG. 4C), rapid and robust nuclear H1.0 methylation (FIG. 4A, panel B, and 4C) accompanied by eviction of met H1.0 into the cytoplasm upon genotoxic-stress induced senescence (FIG. 44, panel C) of bleomycine-treated hADSCs.

Figure 4A:
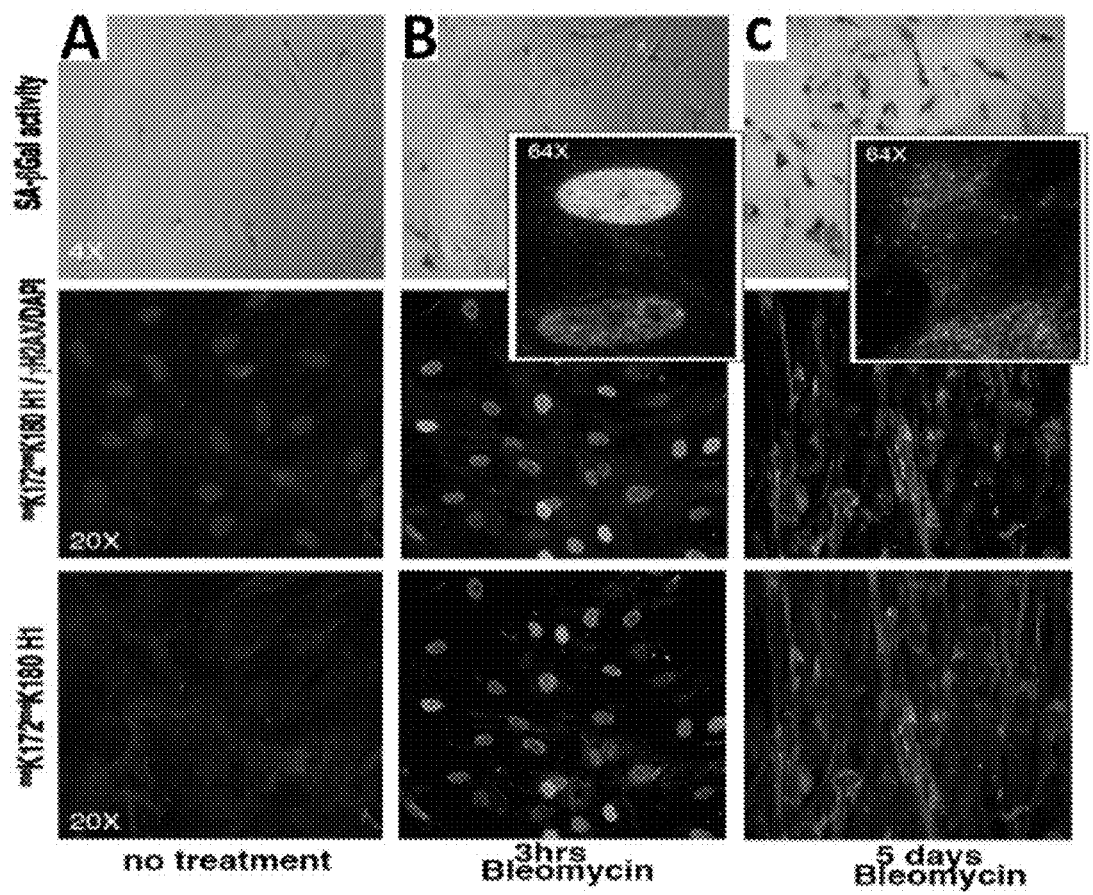
FIGS. 4A-4C illustrate the dynamics of the meK172meK180 methylation of hi stone H1.0 upon genotoxic stress-induced senescence of human adult stem (hADSC).
Figure 4B:
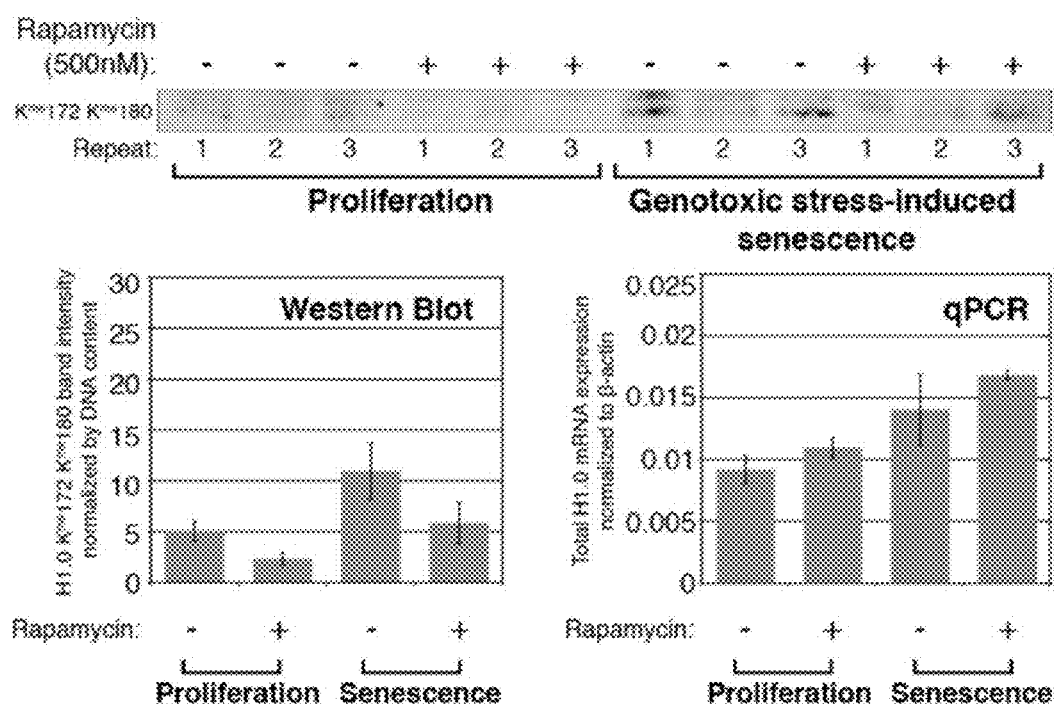
Figure 4C:
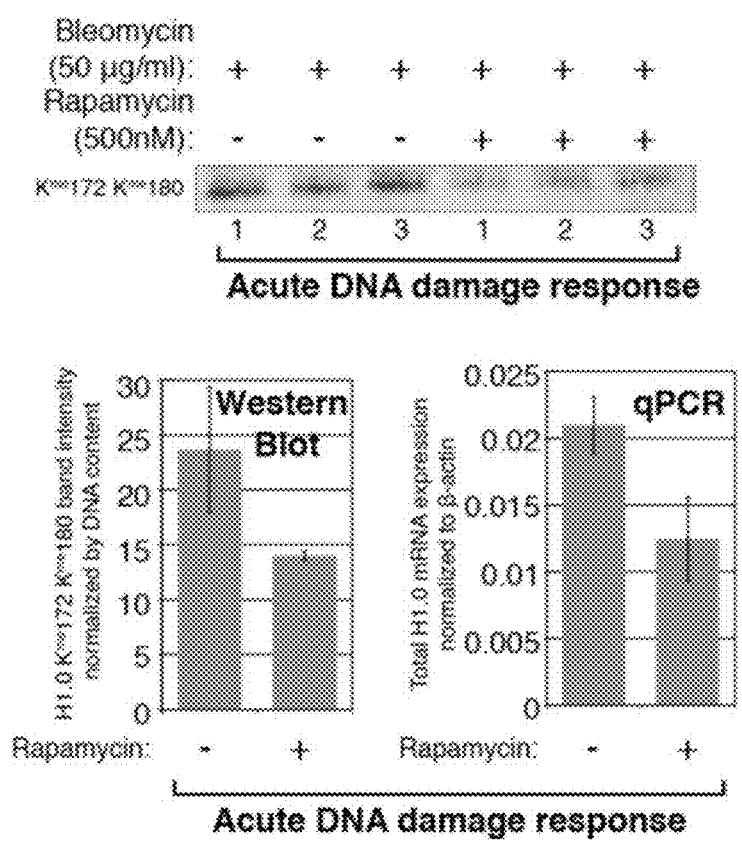
Figure 5A:
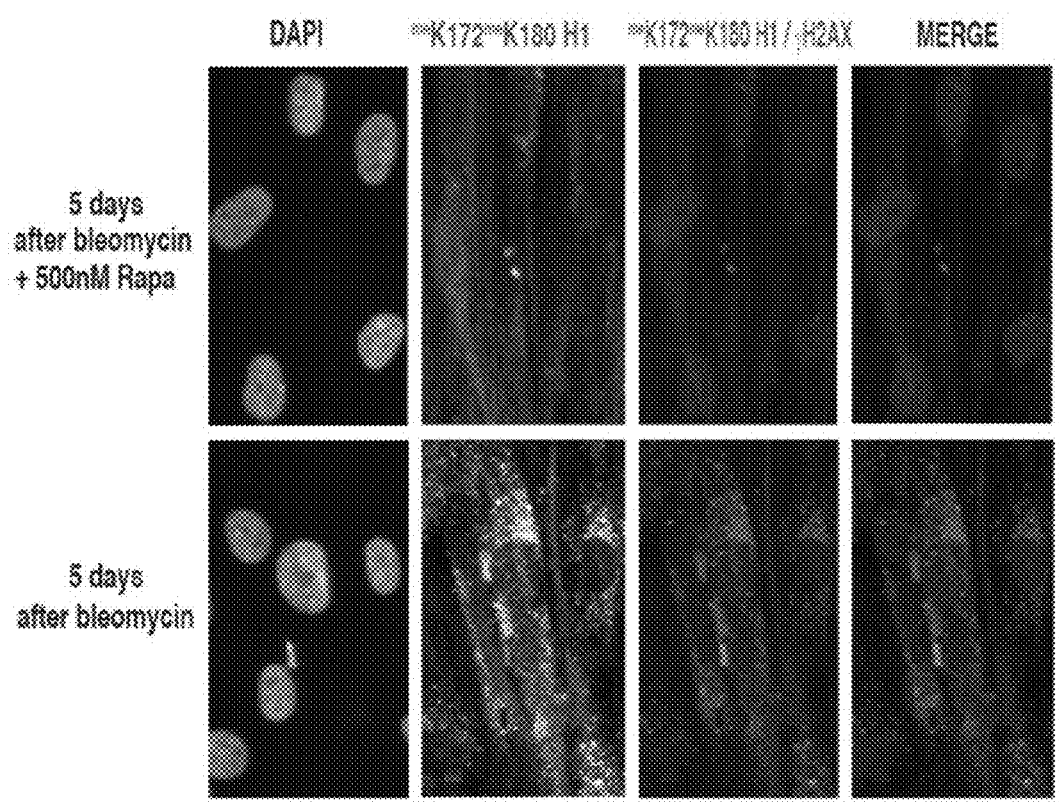
FIGS. 5A-5C illustrate that treatment with rapamycin (500 nM) rescues the cytoplasmic deposition of meK172meK180 methylated form H1.0 upon genotoxic stress-induced senescence of hADSCs. The same experimental conditions were used in this experiment as shown in FIG. 4. Rapamycin treatment reduces H1.0 methylation upon genotoxic-stress induced senescence and acute DDR in primary somatic cells (HCA2).
Figure 5B:
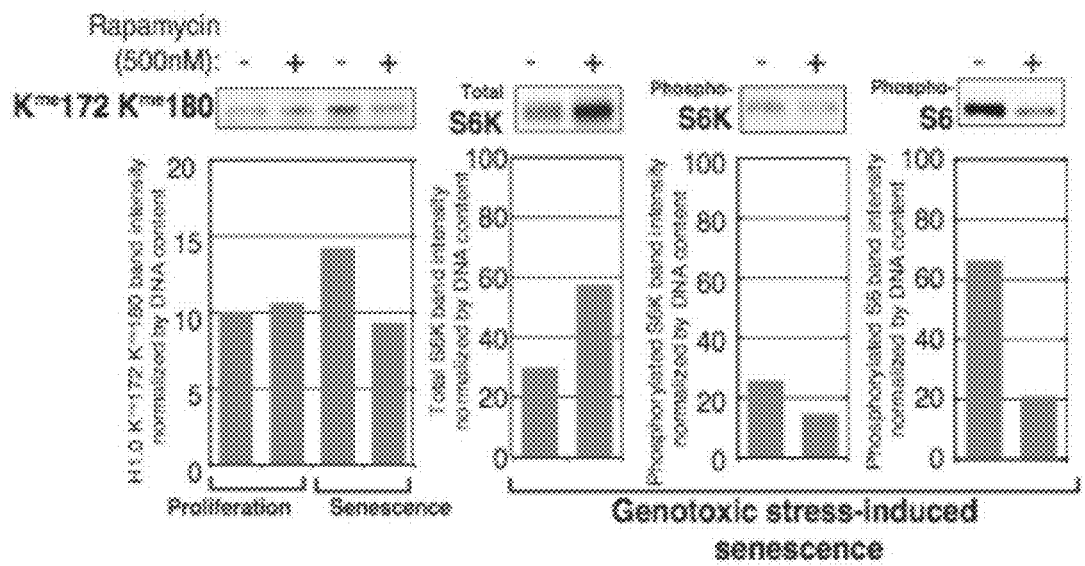
Figure 5C:
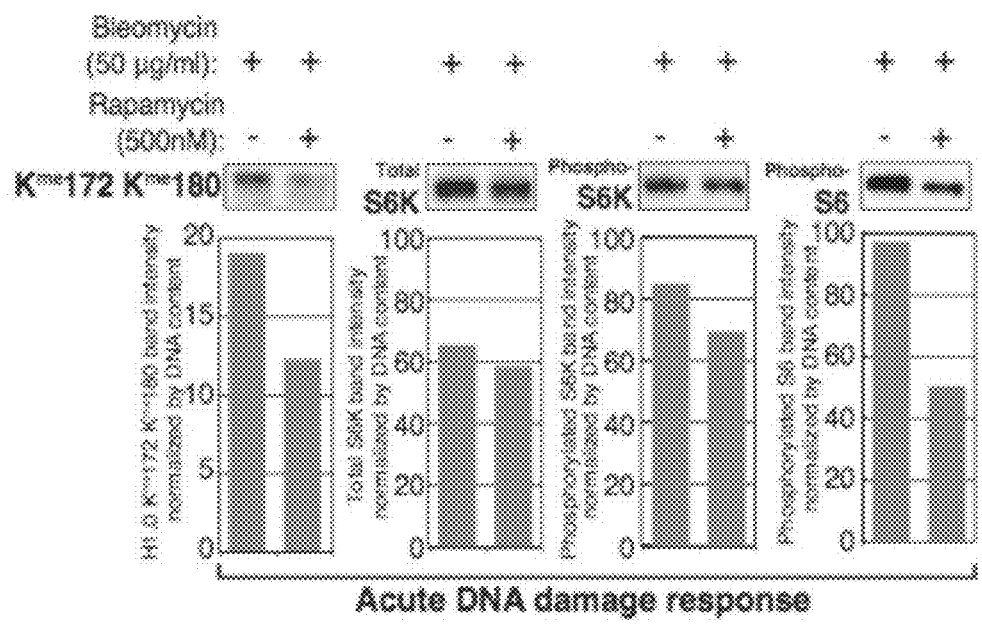

The $^{me}$K172$^{me}$K180 H1.0 forms co-localize with γH2AX, associated with DNA double-stranded breaks (FIG. 4A, panel B). Similar effects were observed in human primary somatic cells, HCA2 (FIGS. 5B and 5C, and data not shown). The IF experiments and Western blot analysis demonstrate that treatment of the either human stem hADSC cells (FIGS. 5A, 4B, and 4C) or somatic HCA2 cells (FIGS. 5B and 5C) with rapamycin (500 nM) 24 hrs prior to bleomicyne-induced DNA damage, decreases $^{me}$K172meK180. This decrease in H1.0 methylation correlates with inhibition of TOR activity (indicted by loss of S6K1 and S6 phosphorylation) within the cells (FIGS. 5 and 5C), and indicates that H1.0 methylation and/or HMT enzymatic activity providing for these PTMs are downstream targets of TOR.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated antibody that specifically binds a methylated histone H1 or a methylated histone H1 isoform comprising one or more methyl groups on H1 residue 172, one or more methyl groups on H1 residue 180, or one or more methyl groups on both residues, or one or more methyl groups on a residue corresponding to H1 residue 172, on a residue corresponding to H1 residue 180, or on residues corresponding to both residues, the H1 residues being numbered relative to human histone H1.0, and wherein said antibodies require the presence of said methyl group(s) for binding to said histones.

2. The antibody of claim 1, wherein H1 residue 172 is mono-, di-, or tri methylated K (lysine).

3. The antibody of claim 1, wherein H1 residue 180 is mono-, di-, or tri methylated K (lysine).

4. The antibody of claim 1, wherein said antibody specifically binds a peptide selected from the group consisting of Ala Lys Pro Val Lys Ala Ser Lys Pro Lys Lys Ala Lys Pro Val meLys Pro Lys Cys (SEQ ID NO:1), Ala Lys Pro Val Lys Ala Ser meLys Pro Lys Lys Ala Lys Pro Val Lys Pro Lys Cys (SEQ ID NO: 2), and Ala Lys Pro Val Lys Ala Ser meLys Pro Lys Lys Ala Lys Pro Val meLys Pro Lys Cys (SEQ ID NO: 3).

5. The antibody of claim 1, wherein the antibody comprises a polyclonal antibody.

6. The antibody of claim 1, wherein the antibody comprises a monoclonal antibody.

7. The antibody of claim 1, wherein the antibody comprises an IgG.

8. The antibody of claim 1, wherein the antibody comprises a Fab.

9. The antibody of claim 1, wherein the antibody comprises a (Fab')$_2$.

10. The antibody of claim 1, wherein the antibody comprises a single chain Fv (scFv).

11. The antibody of claim 1, wherein the antibody comprises a (scFv')$_2$.

12. The antibody of claim 1, wherein said antibody binds to a translationally modified mammalian H1 histone.

13. The antibody of claim 12, wherein said antibody binds to a human metH1.

14. The antibody of claim 1, wherein said antibody is attached to a detectable label.

15. The antibody of claim 14, wherein said antibody is attached to a label selected from the group consisting of a spin label, a colorimetric label, a radioactive label, an enzymatic label, a fluorescent label, and a magnetic label.

16. A kit for determining the level of histone H1 methylation, said kit comprising:
a container containing a first antibody according to claim 1;
optionally a secondary antibody directed against said first antibody; and
optionally reagents for the measurement of a signal derived from an antibody binding to methylated H1 histone.

* * * * *